US012790212B2

(12) United States Patent
Kikuchi et al.

(10) Patent No.: US 12,790,212 B2
(45) Date of Patent: Nov. 10, 2026

(54) ACTIVE OXYGEN SUPPLY DEVICE

(71) Applicant: CANON KABUSHIKI KAISHA, Tokyo (JP)

(72) Inventors: Yuichi Kikuchi, Shizuoka (JP); Masatsugu Hongo, Shizuoka (JP); Atsushi Uematsu, Shizuoka (JP); Masaki Ozawa, Shizuoka (JP); Takumi Furukawa, Shizuoka (JP); Kazuhiro Yamauchi, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 280 days.

(21) Appl. No.: 18/751,473

(22) Filed: Jun. 24, 2024

(65) Prior Publication Data

US 2024/0343571 A1 Oct. 17, 2024

Related U.S. Application Data

(63) Continuation of application No. PCT/JP2022/048046, filed on Dec. 26, 2022.

(30) Foreign Application Priority Data

Dec. 28, 2021 (JP) ................................ 2021-215343
Dec. 21, 2022 (JP) ................................ 2022-203879

(51) Int. Cl.
*A62B 7/08* (2006.01)
*A61L 2/20* (2006.01)
(Continued)

(52) U.S. Cl.
CPC ............ *C01B 13/0203* (2013.01); *A61L 2/20* (2013.01); *A61L 9/20* (2013.01); *H05H 1/2418* (2021.05);
(Continued)

(58) Field of Classification Search
CPC .... A61L 2/14; A61L 9/015; A61L 9/20; B01J 19/08; G03G 5/00; H05H 1/46; C01B 13/10; C01B 13/02
(Continued)

(56) References Cited

U.S. PATENT DOCUMENTS 5,149,375 A 9/1992 Matsuyama
5,849,455 A 12/1998 Ueda et al.
(Continued)

FOREIGN PATENT DOCUMENTS

CN 1040063 A 2/1990
CN 1132800 A 10/1996
(Continued)

OTHER PUBLICATIONS

First Office Action in Chinese Application No. 202280086546.6 (Mar. 2026).
(Continued)

*Primary Examiner* — Monzer R Chorbaji
(74) *Attorney, Agent, or Firm* — Venable LLP

(57) ABSTRACT

An active oxygen supply device equipped with a cylindrical housing having a first opening and a second opening opposite to the first opening, a plasma actuator arranged in the housing, and an ozone decomposition device, in which the plasma actuator causes dielectric barrier discharge to blow out an induction flow, the plasma actuator is arranged such that the blow direction of the induction flow faces the second opening, an air flow that flows from the first opening to the second opening is generated in the housing by the action of the induction flow, the ozone decomposition device decomposes the ozone contained in the air flow to generate active oxygen in the air flow, and the plasma actuator and the ozone decomposition device are arranged such that the air flow containing the active oxygen can flow out to the exterior of
(Continued)

the active oxygen supply device through the second opening.

15 Claims, 17 Drawing Sheets

(51) Int. Cl.

| | |
|---|---|
| ***A61L 9/20*** | (2006.01) |
| ***B01J 19/08*** | (2006.01) |
| ***C01B 13/02*** | (2006.01) |
| ***H05H 1/24*** | (2006.01) |

(52) U.S. Cl.
CPC ........ *H05H 1/2425* (2021.05); *A61L 2202/11* (2013.01); *H05H 2245/36* (2021.05); *H05H 2245/40* (2021.05)

(58) Field of Classification Search
USPC ....... 422/121, 125, 186, 18.04, 186.07, 305; 430/128; 315/111.21
See application file for complete search history.

(56) References Cited

U.S. PATENT DOCUMENTS

| | | | | |
|---|---|---|---|---|
| 7,382,087 | B2 | 6/2008 | Tabata et al. | |
| 7,510,600 | B2 | 3/2009 | Ibe et al. | |
| 7,771,797 | B2 | 8/2010 | Tabata et al. | |
| 8,400,751 | B2 | 3/2013 | Tanaka et al. | |
| 9,295,967 | B2 | 3/2016 | Nakamura et al. | |
| 9,468,698 | B2 | 10/2016 | Ui et al. | |
| 2006/0207428 | A1* | 9/2006 | Ibe | F01N 3/0275 96/74 |
| 2007/0053805 | A1 | 3/2007 | Kaneko et al. | |
| 2016/0151530 | A1* | 6/2016 | Kawanabe | H01T 23/00 422/123 |
| 2017/0007958 | A1 | 1/2017 | Ui et al. | |
| 2019/0145443 | A1 | 5/2019 | Smullin et al. | |
| 2019/0282722 | A1* | 9/2019 | Ui | A61L 9/014 |
| 2023/0139536 | A1 | 5/2023 | Furukawa et al. | |
| 2023/0146111 | A1 | 5/2023 | Furukawa et al. | |
| 2023/0158452 | A1 | 5/2023 | Otsuka et al. | |
| 2023/0226235 | A1 | 7/2023 | Oguma et al. | |
| 2024/0157006 | A1 | 5/2024 | Furukawa et al. | |
| 2024/0157011 | A1 | 5/2024 | Furukawa et al. | |

FOREIGN PATENT DOCUMENTS

| | | | |
|---|---|---|---|
| CN | 1774394 | A | 5/2006 |
| CN | 1935325 | A | 3/2007 |
| CN | 101142022 | A | 3/2008 |
| CN | 103636294 | A | 3/2014 |
| CN | 103857620 | A | 6/2014 |
| CN | 208462123 | U | 2/2019 |
| JP | 52-3872 | A | 1/1977 |
| JP | 63-63232 | B2 | 12/1988 |
| JP | 64-25865 | A | 1/1989 |
| JP | 64-25866 | A | 1/1989 |
| JP | 3-109203 | A | 5/1991 |
| JP | 6-335518 | A | 12/1994 |
| JP | 10-328279 | A | 12/1998 |
| JP | 3060428 | U | 8/1999 |
| JP | 2001-137319 | A | 5/2001 |
| JP | 2004-134671 | A | 4/2004 |
| JP | 2004-236613 | A | 8/2004 |
| JP | 2004-335411 | A | 11/2004 |
| JP | 2005-13840 | A | 1/2005 |
| JP | 2005-80808 | A | 3/2005 |
| JP | 2006-75402 | A | 3/2006 |
| JP | 2006-247582 | A | 9/2006 |
| JP | 2006-257948 | A | 9/2006 |
| JP | 2007-598 | A | 1/2007 |
| JP | 2008-289801 | A | 12/2008 |
| JP | 2009-238519 | A | 10/2009 |
| JP | 2010-194439 | A | 9/2010 |
| JP | 2010-229492 | A | 10/2010 |
| JP | 2011-242091 | A | 12/2011 |
| JP | 2014-9796 | A | 1/2014 |
| JP | 2014-73482 | A | 4/2014 |
| JP | 2015-070921 | A | 4/2015 |
| JP | 2015-182004 | | 9/2015 |
| JP | 2015-182004 | A | 10/2015 |
| JP | 2017-18901 | | 7/2016 |
| JP | 2017-18901 | A | 1/2017 |
| JP | 2019-155006 | | 8/2018 |
| JP | 2021-506443 | | 7/2019 |
| JP | 2019-155006 | A | 9/2019 |
| JP | 2019-180472 | A | 10/2019 |
| JP | 2019-209170 | A | 12/2019 |
| JP | 2020-205215 | A | 12/2020 |
| JP | 2021-506443 | A | 2/2021 |
| KR | 10-2007-0088290 | A | 8/2007 |
| KR | 10-2018-0075727 | A | 7/2018 |
| KR | 10-2113925 | B1 | 5/2020 |
| KR | 10-2267005 | B1 | 6/2021 |
| KR | 10-2021-0152653 | A | 12/2021 |
| WO | 2015/015587 | A1 | 2/2015 |
| WO | WO 2015/015587 | | 1/2016 |
| WO | 2019/132991 | A1 | 7/2019 |
| WO | 2020/089763 | A1 | 5/2020 |
| WO | 2021/256450 | A1 | 12/2021 |
| WO | 2022/004763 | A1 | 1/2022 |
| WO | 2022/004771 | A1 | 1/2022 |
| WO | 2022/092325 | A1 | 5/2022 |
| WO | WO 2021/256450 | | 10/2022 |
| WO | WO 2022/004763 | | 12/2022 |
| WO | WO 2022/004771 | | 12/2022 |
| WO | WO 2022/092325 | | 3/2023 |
| WO | 2023/127822 | A1 | 7/2023 |
| WO | 2023/127823 | A1 | 7/2023 |
| WO | 2023/127831 | A1 | 7/2023 |
| WO | 2023/127832 | A1 | 7/2023 |
| WO | 2023/127833 | A1 | 7/2023 |
| WO | 2023/127836 | A1 | 7/2023 |
| WO | 2023/127837 | A1 | 7/2023 |
| WO | 2023/127838 | A1 | 7/2023 |
| WO | 2023/127839 | A1 | 7/2023 |

OTHER PUBLICATIONS

Kikuchi et al., U.S. Appl. No. 18/751,449, filed Jun. 24, 2024.
Furukawa et al., U.S. Appl. No. 18/751,455, filed Jun. 24, 2024.
Kaneko et al., U.S. Appl. No. 18/751,461, filed Jun. 24, 2024.
Uematsu et al., U.S. Appl. No. 18/751,465, filed Jun. 24, 2024.
Goto et al., U.S. Appl. No. 18/751,446, filed Jun. 24, 2024.
Hongo et al., U.S. Appl. No. 18/751,480, filed Jun. 24, 2024.
Takashima et al., U.S. Appl. No. 18/751,487, filed Jun. 24, 2024.
Furukawa et al., U.S. Appl. No. 18/751,500, filed Jun. 24, 2024.
U.S. Appl. No. 18/751,449, filed Jun. 24, 2024, PCT/JP2022/048043, WO 2023/127836.
U.S. Appl. No. 18/751,455, filed Jun. 24, 2024, PCT/JP/2022/048035, WO 2023/127833.
U.S. Appl. No. 18/751,461, filed Jun. 24, 2024, PCT/JP2022/048044, WO 2023/127837.
U.S. Appl. No. 18/751,465, filed Jun. 24, 2024, PCT/JP2022/048032, WO 2023/127831.
U.S. Appl. No. 18/751,446, filed Jun. 24, 2024, PCT/JP2022/048034, WO 2023/127832.
U.S. Appl. No. 18/751,480, filed Jun. 24, 2024, PCT/JP2022/048047, WO 2023/127839.
U.S. Appl. No. 18/751,487, filed Jun. 24, 2024, PCT/JP2022/047987, WO 2023/127822.
U.S. Appl. No. 18/751,500, filed Jun. 24, 2024, PCT/JP2022/047991, WO 2023/127823.
Masanobu Wakasa et al., "Magnetic Field Effect on the Photocatalytic Reaction with TiO2 Semiconductor Film," 69(4) Journal of The Society of Photographic Science and Technology of Japan 271-275 (2006).

(56) References Cited

OTHER PUBLICATIONS

International Search Report in International Application No. PCT/JP2022/048046 (Mar. 2023).

* cited by examiner

ACTIVE OXYGEN SUPPLY DEVICE

CROSS-REFERENCE TO RELATED APPLICATION

This is a continuation of International Application No. PCT/JP2022/048046, filed on Dec. 26, 2022, and designated the U.S., and claims priority from Japanese Patent Application No. 2021-215343 filed on Dec. 28, 2021, and Japanese Patent Application No. 2022-203879 filed on Dec. 21, 2022, the entire contents of which are incorporated herein by reference.

BACKGROUND OF THE INVENTION

Technical Field of the Invention

The present disclosure is directed to an active oxygen supply device.

Description of the Related Art

Japanese Patent Application Publication No. H06-335518 discloses a nascent oxygen generating device including a device main body disposed at a place where air flows, formed in a cylindrical shape which allows a portion of the air to pass through the inside thereof and having an inner surface thereof made of a metal with a high UV reflectivity, a UV lamp disposed on a shaft inside of the device main body to emit UV light that decomposes ozone, and an ozone generator provided on an upstream side in an air flow inside of the device main body to convert oxygen in the air introduced into the main body to ozone by electric discharge.

In the paragraph [0016] in Japanese Patent Application Publication No. H06-335518, it is stated that such a nascent oxygen generating device improves ozone generation and decomposition capabilities and allows a large amount of nascent oxygen to be generated from the ozone, and the generated nascent oxygen is diffused in a freezing chamber to oxidatively decompose a malodorous substance inside of the freezing chamber and deodorize the inside of the freezing chamber.

SUMMARY OF THE INVENTION

According to study conducted by the present inventors, a capability of supplying the nascent oxygen (hereinafter referred to also as the "active oxygen") from the nascent oxygen generating device according to Japanese Patent Application Publication No. H06-335518 is limited.

At least one aspect of the present disclosure is directed to providing an active oxygen supply device which can more efficiently supply active oxygen to an object to be treated.

At least one embodiment of the present disclosure is directed toward providing an active oxygen supply device comprising:

a cylindrical housing having a first opening and a second opening opposite to the first opening;

a plasma actuator disposed in the housing; and an ozone decomposing device, wherein the plasma actuator has a first electrode, a dielectric material, and a second electrode, the dielectric material is interposed between the first electrode and the second electrode to electrically insulate the first electrode and the second electrode from each other, the first electrode is an exposed electrode provided on a first surface, which is one surface of the dielectric material, the plasma actuator causes a dielectric barrier discharge directed from the first electrode to the second electrode by applying a voltage between the first electrode and the second electrode and causes an induced flow containing ozone to be blown out from the first electrode in a first direction, which is one direction along the surface of the dielectric material, the plasma actuator is disposed such that a direction in which the induced flow is blown out faces the second opening, and causes the induced flow to cause an air flow directed from the first opening to the second opening inside of the housing, the ozone decomposing device decomposes the ozone contained in the air flow to generate active oxygen in the air flow, and the air flow results in an air flow containing the active oxygen, and the plasma actuator and the ozone decomposing device are arranged such that the air flow containing the active oxygen flows out from the second opening to the outside of the active oxygen supply device.

Also, at least one embodiment of the present disclosure is directed toward providing an active oxygen supply device comprising:

a cylindrical housing having a first opening and a second opening opposite to the first opening; and an ozone decomposing device, wherein the cylindrical housing includes a dielectric material, in a cross section of the cylindrical housing in a direction along an axial direction thereof, a first electrode, which is an exposed electrode provided to cover a portion of an inner surface of the cylindrical housing, is disposed on the inner surface, while a second electrode electrically insulated from the first electrode via the dielectric material is disposed externally of the inner surface of the housing, the active oxygen supply device causes a dielectric barrier discharge directed from the first electrode to the second electrode by applying a voltage between the first electrode and the second electrode and causes an induced flow containing ozone to be blown out from the first electrode in a direction of the second opening, which is one direction along the inner surface of the housing, the induced flow causes an air flow directed from the first opening to the second opening inside of the cylindrical housing, the ozone decomposing device decomposes the ozone contained in the air flow to generate active oxygen in the air flow, and the air flow results in an air flow containing the active oxygen, and the first electrode, the second electrode, and the ozone decomposing device are arranged such that the air flow containing the active oxygen flows out from the second opening.

Furthermore, at least one embodiment of the present disclosure is directed toward providing an active oxygen supply device comprising:

a cylindrical housing having a first opening and a second opening opposite to the first opening; and an ozone decomposing device, wherein the cylindrical housing includes a dielectric material, in a cross section of the cylindrical housing in a direction along an axial direction thereof, a first electrode, which is an exposed electrode provided to cover a portion of an inner surface of the cylindrical housing, is disposed on the inner surface, while a second electrode electrically insulated from the first electrode via the dielectric material is disposed externally of the inner surface of the housing, the active oxygen supply device causes a dielectric barrier discharge directed from the first electrode to the second electrode by applying a voltage between the first electrode and the second electrode and causes an induced flow containing ozone to be blown out from the first electrode in a direction of the second opening, which is one direction along the inner surface of the housing, the induced flow causes an air flow directed from the first opening to the second opening inside of the cylindrical housing, the first electrode and the second electrode are arranged such that the air flow containing the ozone flows out from the second opening, and the ozone decomposing device decomposes the ozone contained in the air flow flown out from the second opening to cause active oxygen in the air flow.

According to at least one aspect of the present disclosure, it is possible to obtain an active oxygen supply device which can more efficiently supply active oxygen to an object to be treated.

Further features of the present invention will become apparent from the following description of exemplary embodiments with reference to the attached drawings.

DESCRIPTION OF THE EMBODIMENTS

Figure 1A:
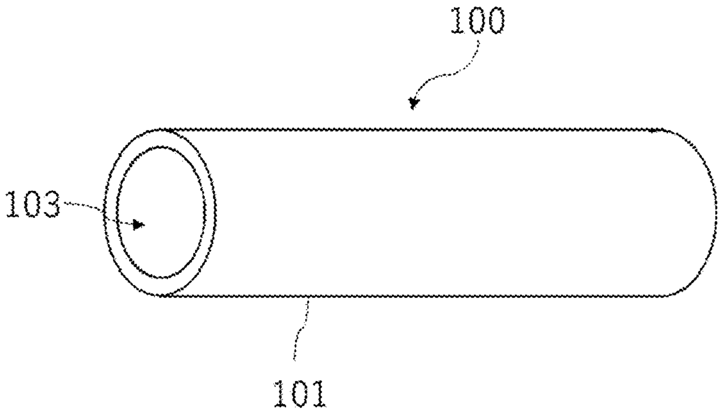
FIG. 1A and FIG. 1B are schematic diagrams of an active oxygen supply device according to an embodiment of the present disclosure.

In the present disclosure, the descriptions of "XX or more and YY or less" or "XX to YY" representing numerical ranges mean numerical ranges including the lower and upper limits, which are endpoints, unless otherwise specified. When numerical ranges are stated stepwise, the upper and lower limits of each numerical range can be combined arbitrarily. In addition, in the present disclosure, wording such as "at least one selected from the group consisting of XX, YY and ZZ" means any of: XX; YY; ZZ; a combination of XX and YY; a combination of XX and ZZ; a combination of YY and ZZ; or a combination of XX and YY and ZZ.

In the present disclosure, "treatment" of an object to be treated with active oxygen is assumed to include all types of treatment that can be carried out with the active oxygen, such as surface modification (hydrophilization treatment), sterilization, deodorization, and bleaching of a surface to be treated of an object to be treated with the active oxygen.

Further, "bacteria" as an object to be subjected to the "sterilization" according to the present disclosure refers to microorganisms, and the microorganisms include fungi, bacteria, unicellular algae, viruses, protozoa, and the like, as well as animal or plant cells (including stem cells, dedifferentiated cells, and differentiated cells), tissue cultures, fused cells obtained by genetic engineering (including hybridomas), dedifferentiated cells, and transformants (microorganisms). Examples of the viruses include norovirus, rotavirus, influenza virus, adenovirus, coronavirus, measles virus, rubella virus, hepatitis virus, herpes virus, HIV virus, and the like. Examples of the bacteria include *Staphylococcus, Escherichia coli, Salmonella, Pseudomonas aeruginosa, Vibrio cholerae, Shigella*, Anthrax, *Mycobacterium tuberculosis, Clostridium botulinum*, Tetanus, *Streptococcus*, and the like. Furthermore, examples of the fungi include *Trichophyton, Aspergillus, Candida*, and the like. Accordingly, the "sterilization" according to the present disclosure includes, for example, even virus inactivation.

In addition, the active oxygen in the present disclosure includes, for example, a free radical caused by decomposition of ozone ($O_3$), such as superoxide ($—O_2^-$) or hydroxy radical (—OH).

Referring to the drawings, modes for carrying out this disclosure will specifically be described below by way of example. Note that dimensions, materials, shapes, relative positioning, and the like of components described in the embodiment are to be appropriately changed depending on configurations of members to which the disclosure is applied and various conditions. In other words, it is not intended to limit the scope of this disclosure to the following modes. Furthermore, in the following description, components having the same functions are denoted by the same numerals in the drawings, and a description thereof may be omitted.

According to the study conducted by the present inventors, a reason for the limited capability of supplying the active oxygen from the nascent oxygen generating device according to Japanese Patent Application Publication No. H06-335518 is presumed as follows. The active oxygen is extremely unstable, and —$O_2$— having an extremely short half-life of $10^{-6}$ seconds and —OH having an extremely short half-life of $10^{-9}$ seconds are considered to be promptly converted to stable oxygen and water.

In particular, it is assumed that the nascent oxygen generating device according to Japanese Patent Application Publication No. H06-335518 is disposed at a place where air flows, and a portion of the air passes through the inside of the cylindrical device main body. Specifically, in FIG. 2 in Japanese Patent Application Publication No. H06-335518, an air flow is caused by a freezer fan 4 placed in the freezing chamber. In such a situation, even when active oxygen is generated inside of the device main body, it can be considered that air flowing into the device main body from the outside forms a turbulent flow therein, and the active oxygen is converted in an extremely short time period to oxygen and water by collision with a wall inside of the device main body or the like due to the turbulent flow. Accordingly, it can be considered that an amount of the active oxygen flowing to the outside of the device main body is extremely limited.

Under such considerations, the present inventors further conducted study with the view to obtaining an active oxygen supply device capable of more positively and reliably supplying active oxygen to an object to be treated, and consequently found that the active oxygen supply device, the active oxygen treatment device, and the active oxygen treatment method (which may be hereinafter referred to also as the "active oxygen supply device and the like") each described above contributed to attainment of the object. A description will be given below of specific embodiments of the active oxygen supply device or the like according to the present disclosure. Note that the active oxygen supply device and the like according to the present disclosure are not limited to the following specific embodiments.

First Embodiment

An active oxygen supply device according to the first embodiment includes a cylindrical housing having a first opening and a second opening opposite to the first opening, a plasma actuator disposed in the housing, and an ozone decomposing device.

In the plasma actuator, a first electrode, a dielectric material, and a second electrode are stacked in this order. Between the first electrode and the second electrode, the dielectric material is interposed to thereby electrically insulate the first electrode and the second electrode from each other.

The first electrode is an exposed electrode provided on a first surface, which is one surface of the dielectric material. By applying a voltage between the first electrode and the second electrode, a dielectric barrier discharge directed from the first electrode to the second electrode is caused, and induced flows containing ozone are blown out from the first electrode in a first direction, which is one direction along a surface of the dielectric material. The plasma actuator is disposed such that a direction in which the induced flows are blown out, which is the first direction, faces the second opening, and uses the induced flows to cause an air flow directed from the first opening to the second opening inside of the housing.

Meanwhile, the ozone decomposing device decomposes the ozone contained in the air flow caused inside of the housing to thereby generate active oxygen in the air flow. Thus, the air flow results in an air flow containing the active oxygen.

Furthermore, the plasma actuator and the ozone decomposing device are arranged such that the air flow containing the active oxygen flows out from the second opening to the outside of the active oxygen supply device.

Using the drawings, the active oxygen supply device according to the present embodiment will be described in greater detail.

Figure 1B:
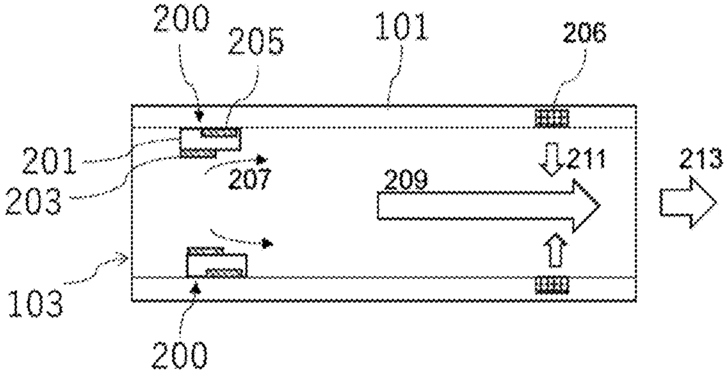

FIG. 1A and FIG. 1B are illustrative views of an active oxygen supply device 100 according to the present embodiment, in which FIG. 1A is a perspective view of a cylindrical housing 101 forming an outer appearance thereof. The cylindrical housing 101 has a first opening 103 in one end portion thereof, while having a second opening not shown in an opposite end portion thereof.

FIG. 1B is a cross-sectional view of the active oxygen supply device 100 in a direction along a direction (hereinafter referred to also as a "longitudinal direction") extending from the first opening to the second opening. On an inner surface of the cylindrical housing 101, a plasma actuator 200 is placed. The plasma actuator 200 has a first electrode 203, which is an exposed electrode provided on one surface of the dielectric material 201, and a second electrode 205 electrically insulated from the first electrode 203 with the dielectric material 201 being interposed therebetween.

Figure 2A:
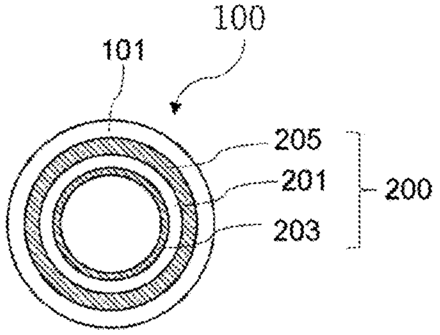
FIG. 2A and FIG. 2B are schematic diagrams of the active oxygen supply device according to an embodiment of the present disclosure.
Figure 2B:
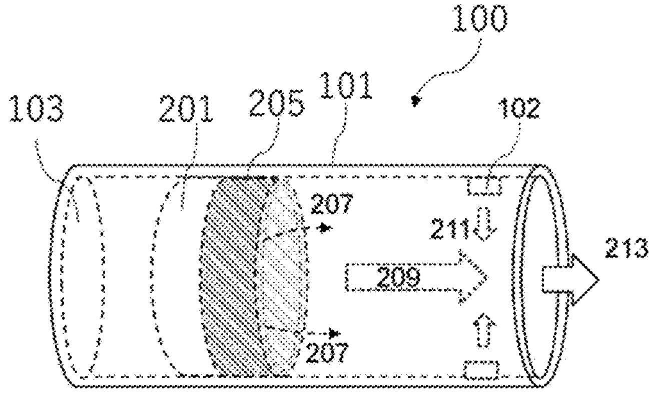

As illustrated in FIG. 2A obtained by viewing the active oxygen supply device 100 from the first opening side thereof and FIG. 2B obtained by seeing through the active oxygen supply device 100, the plasma actuator 200 is preferably disposed around an entire circumference in a circumferential direction of the inner surface of the cylindrical housing 101.

Then, a voltage is applied between the first electrode 203 and the second electrode 205 to cause a dielectric barrier discharge directed from the first electrode to the second electrode, and induced flows 207 containing ozone are blown out from the first electrode in the first direction, which is the one direction along the first surface being one surface of the dielectric material.

By the induced flows 207 containing the ozone, an air flow containing the ozone is caused in a direction indicated by an arrow 209 inside of the cylindrical housing 101, and air outside of the active oxygen supply device is retrieved from the first opening 103 into the cylindrical housing 101. The air flow 209 flows out from the second opening to the outside of the active oxygen supply device.

Figure 4A:
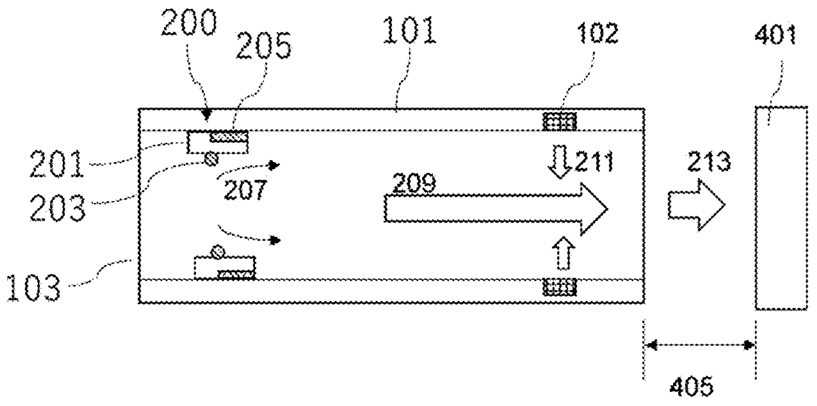
FIG. 4A and FIG. 4B are schematic diagrams of the active oxygen supply device according to an embodiment of the present disclosure.

In addition, in the cylindrical housing 101, a UV light source 102 is provided as the ozone decomposing device 102 downstream in each of the induced flows 207 and the air flow 209. The UV light source 102 irradiates the air flow 209 containing the ozone with UV light 211. Thus, it is possible to allow the UV light 211 to decompose the ozone in the air flow 209 and generate active oxygen 213 in the air flow 209, and the air flow 209 results in an air flow containing the active oxygen. The air flow 213 containing the active oxygen flows out from the second opening to the outside of the housing. As a result, the active oxygen is supplied to a to-be-treated object 401 (FIG. 4A). When the ozone decomposing device 102 is, e.g., a heating device or a humidifying device also, the ozone decomposing device 102 may similarly decompose the ozone in the air flow 209 with heat or moisture and supply the air flow 213 containing the active oxygen.

In the active oxygen supply device according to the present disclosure, in the cylindrical housing 101, the plasma actuator 200 is disposed to cause the induced flows to blow out in a direction facing the second opening in the housing, and uses the induced flows to cause the air flow directed from the first opening to the second opening in the housing.

According to the study conducted by the present inventors, it can be considered that the active oxygen contained in the air flow 209 generated inside of the housing due to the induced flows from the plasma actuator can maintain an active state thereof over a period longer than a generally termed lifetime of active oxygen (half-life of —$O_2^-$: $10^{-6}$ seconds, half-life of —OH: $10^{-9}$ seconds). A conceivable reason why the active oxygen generated in the air flow can maintain activity over a long period is that, since the air flow 209 generated in the housing due to the induced flows, which are unidirectional jet streams, are extremely regulated flows unlike air flows forcibly introduced into the housing by a fan placed outside of the device or the like, the active oxygen is protected in the air flow 209, and deactivation resulting from collision with an inner wall of the housing or the like is extremely unlikely to occur.

Consequently, the active oxygen is maintained from upstream to downstream in the air flow 209 without being deactivated, and it is possible to further increase a probability per unit time that a malodorous substance or bacteria present on a surface of the object to be treated comes into contact with the active oxygen.

Therefore, in the active oxygen supply device according to the present disclosure, it is preferable to minimize formation of an air flow that disturbs the air flow 209 resulting from the induced flows formed in the housing. Accordingly, it is preferable not to place another air flow generating device (such as, e.g., a ventilation fan) which causes the air flow that disturbs the air flow 209 inside the housing or outside the housing.

In addition, the plasma actuator 200 preferably has a shape along the inner surface of the cylindrical housing 101. When the cylindrical housing 101 is viewed from the second opening, the plasma actuator 200 may be provided on a portion of the inner surface of the cylindrical housing 101 in the circumferential direction or a plurality of the plasma actuators 200 may also be provided on a portion of the inner surface of the cylindrical housing 101 in the circumferential direction. For example, when the cylindrical housing 101 is viewed from the second opening, a ratio of a length over which the plasma actuators 200 are provided to an entire length of the inner surface of the cylindrical housing 101 in the circumferential direction is preferably 30% or more, 50% or more, 70% or more, 80% or more, 90% or more, or 95% or more, with an upper limit thereof being 100% or less.

When the plurality of plasma actuators 200 are provided on a portion in the circumferential direction, the plasma actuators 200 are preferably provided at substantially the same positions in the longitudinal direction. The "substantially the same" means that the plasma actuators 200 need only to be at the same positions to a degree that the induced flows 207 join together.

When the cylindrical housing 101 is viewed from the second opening, the plurality of plasma actuators 200 are preferably provided to be rotationally symmetric. For example, the plasma actuators 200 are preferably provided to be twofold to sixfold symmetric.

Moreover, the plasma actuator 200 is preferably positioned around the entire circumference in the circumferential direction of the cylindrical housing 101. Such positioning allows the induced flows 207 containing the ozone to be simultaneously blown out in the same direction. As a result, the induced flows 207 in the cylindrical housing 101 join together to generate the air flow 209 having a larger driving force.

Since the air flow 209 has a high driving force, a driving force of the active oxygen 213 generated by the irradiation with the UV light 102 is also increased. Consequently, it is possible to more efficiently supply the active oxygen to the surface of the object to be treated.

A detailed description will be given below of the plasma actuator 200.

<First Electrode and Second Electrode>

Materials for forming the first electrode and the second electrode are not particularly limited as long as the materials have excellent conductivities. For example, a metal such as copper, aluminum, stainless steel, gold, silver, or platinum, a plated or vapor-deposited metal, a conductive carbon material such as carbon black, graphite, or carbon nanotube, a composite material obtained by mixing the conductive carbon material with a resin or the like can be used. The material forming the first electrode and the material forming the second electrode may be the same or different.

Among these, aluminum, stainless steel, or silver which is resistant to corrosion and excellent in discharge uniformity is preferred.

As shapes of the first electrode and the second electrode, a flat plate shape, a wire shape, a needle shape, and the like can be used without particular limitation. The shape of the first electrode is preferably a flat plate shape. Meanwhile, the shape of the second electrode is preferably a flat plate shape. When at least one of the first electrode and the second electrode has a flat plate shape, an aspect ratio (Length of Long Side/Length of Short Side) of the flat plate is preferably 2 or more.

<Dielectric Material>

The dielectric material is not particularly limited as long as the dielectric material is a material having a high electrically insulating property. For example, resins such as polyimide, polyester, a fluorine resin, a silicone resin, an acrylic resin, and a phenol resin, glass, ceramics, composite materials obtained by mixing these with resins or the like, and the like can be used.

In a case where the plasma actuator is disposed around the entire circumference in the circumferential direction of the inner surface of the housing having a cylindrical shape as illustrated in FIGS. 2A and 2B, the dielectric material made of a flexible resin, such as polyimide or a silicone resin, is preferable. In particular, the silicon resin having bendability in addition to the flexibility can be disposed even on a housing having a complicated shape with excellent followability, and is therefore particularly preferable.

<Plasma Actuator>

The plasma actuator is not particularly limited as long as the plasma actuator has the first electrode and the second electrode which are provided with the dielectric material being interposed therebetween and can cause induced flows, which are the unidirectional jet streams containing ozone, by applying a voltage between the two electrodes.

In the plasma actuator, as a shortest distance between the first electrode and the second electrode is shorter, a plasma is more likely to be generated. Accordingly, a film thickness of the dielectric material is preferably as small as possible as long as the film thickness is within a range in which no electric breakdown occurs, and can be set to 10 μm to 1000 μm, or preferably 10 μm to 200 μm. Meanwhile, the shortest distance between the first electrode and the second electrode is preferably 200 μm or less, or more preferably 50 μm to 200 μm.

Figure 3:
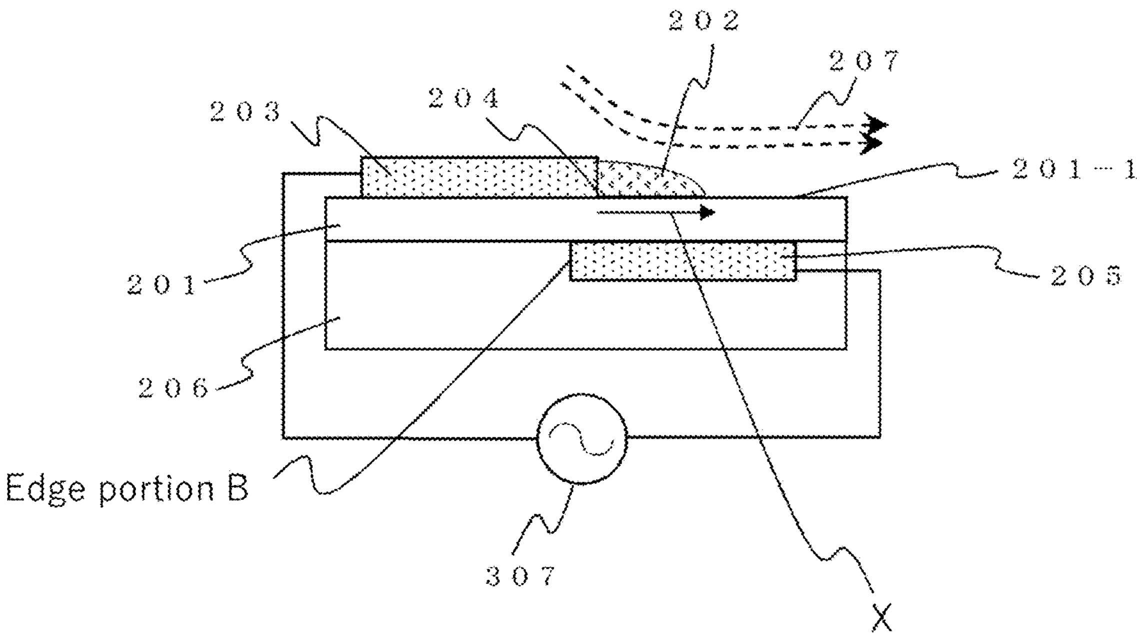
FIG. 3 is an illustrative view of a plasma actuator according to an embodiment of the present disclosure.

FIG. 3 illustrates a cross-sectional structure of an embodiment of the plasma actuator 200. The plasma actuator is a so-called DBD (Dielectric Barrier Discharge) plasma actuator (which may be hereinafter referred to simply as "DBD-PA") in which, on one surface (hereinafter referred to also as the "first surface") of the dielectric material 201, the exposed electrode (hereinafter referred to also as the "first electrode") 203 having an exposed end surface is provided while, on a surface (hereinafter referred to also as the "second surface") opposite to the first surface, the second electrode 205 is provided. In FIG. 3, a reference sign 206 denotes a dielectric substrate for embedding the second electrode 205 in a thickness direction of the plasma actuator so as to prevent induced flows from an end surface of the second electrode from being formed. Between the first electrode and the second electrode, a voltage can be applied by a power source 307.

In the plasma actuator 200, the first electrode 203 and the second electrode 205, which are arranged with the dielectric material 201 being interposed therebetween, are positioned to be, e.g., displaced from each other, while obliquely facing each other. By applying the voltage from the power source 307 between these electrodes (between the two electrodes), the dielectric barrier discharge directed from the first electrode 203 to the second electrode 205 is generated. Then, in a direction (X-direction in FIG. 3) in which the second electrode extends, a plasma 202 is generated from an edge portion 204 of the first electrode 203 along an exposed portion (portion uncovered with the first electrode) 201-1 of the first surface of the dielectric material 201.

At the same time, an air intake flow directed from a space inside of the housing to the electrodes is also generated. Electrons in the surface plasma 202 collide with oxygen molecules in air to dissociate the oxygen molecules and cause oxygen atoms. The resulting oxygen atoms collide with undissociated oxygen molecules to generate ozone. Consequently, by the action of a jet-stream flow resulting from the surface plasma 202 and the air intake flow, the induced flows 207 containing high-concentration ozone are generated from the edge portion 204 of the first electrode 203 along the surface of the dielectric material 201.

In other words, the plasma actuator includes the first electrode 203, the dielectric material 201, and the second electrode 205 which are stacked in this order, and the first electrode 203 is the exposed electrode provided on the first surface of the dielectric material 201. Then, the plasma actuator causes the dielectric barrier discharge directed from the first electrode 203 to the second electrode 205 by applying the voltage between the first electrode 203 and the second electrode 205 and causes the induced flows to be blown out from the first electrode 203 in the first direction (X-direction in FIG. 3) which is one direction along the first surface of the dielectric material 201.

More specifically, the dielectric barrier discharge directed from the one edge portion 204 of the first electrode 203 to the second electrode 205 is caused, and the induced flows, which are unidirectional jet streams, are blown out from the one edge portion 204 of the first electrode 203 in the first direction (X-direction in FIG. 3) along the first surface of the dielectric material 201.

Meanwhile, in a cross section along the thickness direction of the plasma actuator, the second electrode 205 is present to extend in the direction (first direction) in which the induced flows are blown out.

More specifically, for example, the plasma actuator has the dielectric material 201 and, when the cross section along the thickness direction of the plasma actuator is viewed, the first electrode 203 and the second electrode 205 are disposed to obliquely face each other via the dielectric material 201 in the thickness direction of the plasma actuator. The first electrode 203 is provided so as to cover a portion of the first surface of the dielectric material 201, and the first surface of the dielectric material has the exposed portion 201-1 uncovered with the first electrode 203. At least one portion of the exposed portion 201-1 and the second electrode 205 have overlap therebetween.

Then, by applying the voltage between the first electrode and the second electrode, from the edge portion 204 of the first electrode 203 in the first direction in the cross section (FIG. 3) along the thickness direction, the induced flows containing ozone are generated along the exposed portion of the dielectric material which overlaps the second electrode 205.

The induced flows result in, e.g., wall surface jet streams along the exposed portion 201-1 to easily supply the high-concentration ozone to specified positions. A length (i.e., a length from the edge portion 204 of the first electrode in the first direction to an end portion of the first surface of the dielectric material) of the exposed portion 201-1 in an induced flow direction is not particularly limited, but is preferably 0.1 to 50 mm, more preferably 0.5 to 20 mm, or still more preferably 1.0 to 10 mm.

Using FIG. 3, a description will be given of the overlap between the first electrode 203 and the second electrode 205 of the plasma actuator, which is the ozone generating device. FIG. 3 is a cross-sectional view of the plasma actuator.

The first electrode 203 and the second electrode 205, which are arranged to obliquely face each other, may also be such that, when viewed from an upper side of the cross section, the edge portion 204 of the first electrode is present in a portion where the second electrode 205 is formed with the dielectric material being interposed therebetween. In other words, the first electrode and the second electrode may also be provided to overlap each other with the dielectric material being interposed therebetween. In this case, it is preferable that, at the time of the voltage application, electric breakdown does not occur in the portion where the first electrode and the second electrode overlap each other with the dielectric material being interposed therebetween.

FIG. 3 illustrates an embodiment in which the first electrode and the second electrode overlap with each other with the dielectric material being interposed therebetween. It is assumed that, in the cross section across the thickness direction of the plasma actuator, the edge portion 204 of the first electrode in the first direction is an edge portion A, and an edge portion of the second electrode in a second direction (opposite to the X-direction) which is reverse to the first direction is an edge portion B. At this time, the edge portion B is preferably located ahead of the edge portion A in the second direction (opposite to the X-direction).

The first electrode and the second electrode thus overlapping each other with the dielectric material being interposed therebetween allow the plasma and the induced flows to be stably generated.

In addition, since the first electrode and the second electrode are disposed to obliquely face each other via the dielectric material 201, the edge portion B is located ahead of the edge portion of the first electrode opposite to the edge portion A in the first direction (X-direction). This can suppress generation of the induced flows from the edge portion of the first electrode opposite to the edge portion A.

Next, an embodiment in which the first electrode and the second electrode do not overlap each other with the dielectric material being interposed therebetween will be shown. In a cross section along the thickness direction of the plasma actuator, when the edge portion 204 of the first electrode in the first direction is assumed to be the edge portion A and the edge portion of the second electrode leading in the second direction (opposite to the X-direction) reverse to the first direction is assumed to be the edge portion B, for example, the edge portion B is located ahead of the edge portion A in the first direction (X-direction).

When the first electrode and the second electrode thus do not overlap each other with the dielectric material being interposed therebetween, to compensate for a weakened electric field due to a relatively increased shortest distance between the electrodes, the voltage to be applied between the two electrodes is preferably relatively increased.

A coincidence between the edge portion A and the edge portion B in the thickness direction of the dielectric material in the cross section along the thickness direction of the plasma actuator is also among preferred embodiments. The mode shows an embodiment in which, e.g., the edge portion A and the edge portion B face each other at a shortest distance with the dielectric material being interposed therebetween, and the first electrode and the second electrode neither overlap with the dielectric material being interposed therebetween nor are away from each other. This allows the energy applied between the two electrodes to be efficiently used to generate the induced flows.

The overlap between the edge portion of the first electrode and the edge portion of the second electrode under the assumption that a length of the overlap is positive is preferably set to −100 μm to +1000 μm, more preferably set to 0 μm to +200 μm, or still more preferably set to 0 μm when viewed from above the cross-sectional view.

A thickness of the electrode is not particularly limited whether the electrode is the first electrode or the second electrode, but can be set to 10 μm to 1000 μm. When the thickness is 10 μm or more, a resistance decreases, and the plasma is likely to be generated. When the thickness is 1000 μm or less, electric field concentration is likely to occur, and consequently the plasma is likely to be generated.

A width of the electrode is not particularly limited whether the electrode is the first electrode or the second electrode, and can be set to 1000 μm or more.

When the edge portion of the second electrode is exposed, the plasma is generated also from the edge portion of the second electrode, and induced flows facing the opposite side of the induced flows 207 derived from the first electrode may be formed. In the active oxygen supply device according to the present embodiment, an ozone concentration in an inner space of the active oxygen supply device other than a surface region of the object to be treated is preferably set as low as possible. In addition, it is preferable to prevent flowing motion of a gas which may disturb the induced flows 207 from being generated in a vessel. Therefore, it is preferable to prevent induced flows derived from the second electrode from being generated.

Accordingly, to prevent a plasma from being generated from the second electrode 205, the second electrode 205 is preferably an embedded electrode. For example, as illustrated in FIG. 1B or FIG. 3, the second electrode may be covered with a dielectric material such as the dielectric substrate 206, or may also be embedded in the dielectric material 201. The second electrode needs only to be embedded to such a degree as to be able to prevent generation of a plasma from the edge portion of the second electrode, and it may also be possible that, e.g., a portion of a surface of the second electrode is exposed, and the exposed surface of the second electrode and the dielectric substrate 206 or the dielectric material 201 form the same plane. Preferably, the edge portion of the second electrode is covered with the dielectric substrate 206 or the dielectric material 201.

Accordingly, for example, the plasma actuator is preferably a SDBD (single dielectric barrier discharge) plasma actuator.

The plasma actuator is preferably such that induced flows are not generated from an edge portion of the first electrode other than the edge portion A thereof defined as described above. Accordingly, the edge portion other than the edge portion A may also be covered with the dielectric material. This allows unidirectional jet streams to be generated even when the first electrode and the second electrode overlap each other in a Y-axis direction. Alternatively, it may also be possible to control shapes of the electrodes and prevent induced flows from being generated from the edge portion other than the edge portion A in relation to the second electrode. For example, when the electrodes have rectangular shapes, it may also be possible to allow the first electrode and the second electrode to have the same lengths in a Z-axis direction (direction perpendicular to a direction in which the induced flows are blown out from the edge portion A) or allow the first electrode to have a longer length in the Z-axis direction. Such an embodiment allows easy control of the directions of the induced flows.

Figure 4B:
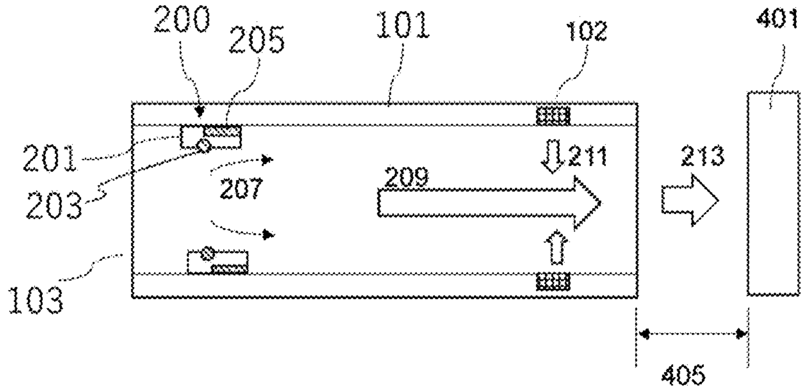

As illustrated in FIG. 4B, the first electrode 203 of the plasma actuator may also be partly embedded in the dielectric material 201 as long as the first electrode 203 is exposed at the surface of the dielectric material 201.

Figure 5A:
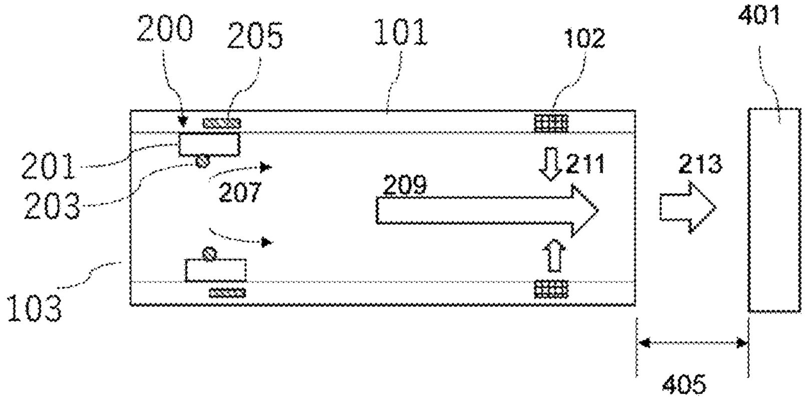
FIG. 5A and FIG. 5B are schematic diagrams of the active oxygen supply device according to an embodiment of the present disclosure.
Figure 5B:
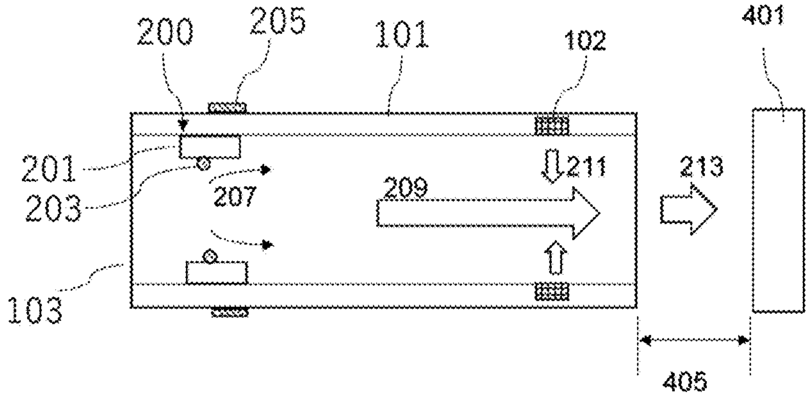

As illustrated in FIG. 5A, the second electrode of the plasma actuator may also be configured to be embedded inside of the cylindrical housing 101. Alternatively, as illustrated in FIG. 5B, the second electrode may also be disposed outside of the cylindrical housing 101.

The induced flows 207 containing the high-concentration ozone flow in a direction of the jet-stream flow resulting from the surface plasma extending from the edge portion 204 of the first electrode 203 along the exposed portion 201-1 of the first surface of the dielectric material 201, i.e., a direction extending from the edge portion 204 of the first electrode 203 along the exposed portion 201-1 of the first surface of the dielectric material. The induced flows are flows of a gas containing the high-concentration ozone and having a speed of about several meters per second to several tens of meters per second.

The voltage to be applied between the first electrode 203 and the second electrode 205 of the plasma actuator is not particularly limited as long as the voltage is in an embodiment which allows the plasma actuator to generate a plasma. The voltage may be either a dc voltage or an ac voltage, but is preferably the ac voltage. Using a pulse voltage as the voltage is also a preferred embodiment.

Furthermore, an amplitude and a frequency of the voltage can be set appropriately to adjust flow rates of the induced flows and ozone concentrations in the induced flows. In this case, a selection may be made appropriately from a viewpoint of generating, in each of the induced flows, an ozone concentration required to generate an effective active oxygen concentration or effective active oxygen amount according to an object of the treatment, supplying the generated active oxygen to the surface region of the object to be treated in a state where the effective active oxygen concentration or effective active oxygen amount according to the object of the treatment are maintained, or the like.

For example, the amplitude of the voltage can be set to 1 kV to 100 kV. In addition, the frequency of the voltage can be set preferably to 1 kHz or more, or more preferably to 10 kHz to 100 kHz.

When the ac voltage is used as the voltage, a waveform of the ac voltage is not particularly limited, and a sine wave, a rectangular wave, a triangular wave, or the like can be used but, from a viewpoint of a rising speed of the voltage, the rectangular wave is preferred.

A duty ratio of the voltage can also be selected appropriately, but the rising speed of the voltage is preferably high. Preferably, the voltage is applied such that the voltage rises from a bottom of the amplitude of a wavelength to reach a top thereof at 400,0000 V/second or more.

Note that a value (voltage/film thickness) obtained by dividing the amplitude of the voltage to be applied between the first electrode 203 and the second electrode 205 by a film thickness of the dielectric material 201 is preferably set to 10 kV/mm or more.

<Ozone Decomposing Device>

The active oxygen supply device or an active treatment device includes the ozone decomposing device 102. The ozone decomposing device decomposes the ozone contained in the air flow 209 to generate active oxygen in the air flow 209. As the ozone decomposing device, an ozone decomposing device that can act on the ozone contained in the air flow and decompose the ozone can be used. As the ozone decomposing device, an ozone decomposing device that can decompose the ozone without disturbing the air flow is preferred.

Preferably, the ozone decomposing device is at least one device selected from the group consisting of a UV light source that irradiates the air flow with UV light to generate active oxygen in the air flow, a heating device that heats the air flow to generate active oxygen in the air flow, and a humidifying device that humidifies the air flow to generate active oxygen in the air flow. The ozone decomposing device may also be a combination thereof. For example, the ozone decomposing device may be a device that heats the air flow, while applying the UV light to the air flow, or may also be a device that humidifies the inside of the housing, while applying the UV light to the air flow and heating the air flow. More preferably, the ozone decomposing device is the UV light source. A description will be given below of each of the devices.

<UV Light Source and UV Light>

The UV light source is not particularly limited as long as the UV light source can emit UV light that can excite the ozone and generate active oxygen. The UV light source is also not particularly limited as long as the UV light source has a wavelength and an illuminance of the UV light which are required to excite the ozone and obtain the effective active oxygen concentration or effective active oxygen amount according to the object of the treatment.

For example, a light absorption spectrum of the ozone has a peak value of 260 nm, and accordingly a peak wavelength of the UV light is preferably 220 nm to 310 nm, more preferably 253 nm to 285 nm, or still more preferably 253 nm to 266 nm.

As a specific UV light source, a low-pressure mercury lamp in which mercury is encapsulated together with an inert gas, such as argon or neon, in quartz glass, a cold cathode tube UV lamp (UV-CCL), a UV LED, or the like can be used. Wavelengths of the low-pressure mercury lamp and the cold cathode tube UV lamp may appropriately be selected from among 254 nm and the like. Meanwhile, from a viewpoint of output performance, a wavelength of the UV LED may appropriately be selected from among 265 nm, 275 nm, 280 nm, and the like.

<Heating Device>

The heating device 102 is not particularly limited as long as the heating device 102 can give thermal energy that can excite the ozone in the air flow 209 and generate active oxygen. Since thermal decomposition of the ozone begins at about 100° C., a device that can heat the air flow 209 to about 120° C. is preferred. Meanwhile, in order to suppress influence of heat resulting from melting, decomposition, or the like of the object to be treated on the object to be treated, a temperature is preferably 200° C. or less. The temperature is preferably 100 to 140° C., or more preferably 110 to 130° C.

The heating device is not particularly limited, and may be, e.g., a device including a heat source that supplies heat (heat supply means), or may also be a device not including the heat source (heat supply means). Specifically, as the heating device including the heat supply means, e.g., a ceramic heater, a cartridge heater, a sheathed heater, an electric heater, an oil heater, or the like can be used. In the case of a device including a metallic heat generator, the heat generator is preferably a material having an excellent oxidation resistance, such as a nichrome-based alloy or tungsten. As the heating device not including the heat supply means, e.g., a device that heats the air flow 209 by dielectric heating (such as microwave heating, electronic heating, RF heating, or wireless frequency heating) can be used. Preferably, the cartridge heater is used.

<Humidifying Device>

The humidifying device 102 is not particularly limited as long as the humidifying device 102 can generate active oxygen in the air flow by humidifying the inside of the housing to cause the air flow 209 to contain water and decomposing the ozone in the air flow with the water. The humidification mentioned herein is giving moisture to a target, and an embodiment of the moisture is not particularly limited and may also be at least one selected from the group consisting of a gas, a liquid, and a solid. As the water to be used when the moisture is given, known water may optionally be used, and a substance other than water may also be contained.

The humidifying device is not particularly limited and, for example, a vaporization-type humidifying device or a mist-type humidifying device can be used.

Preferably, the humidifying device has a directivity with respect to a direction in which the moisture is supplied (hereinafter also referred to simply as the directivity) so as not to increase a humidity in the vicinity of the plasma actuator. By having the directivity, the humidifying device can efficiently humidify the vicinity of the air flow 209 or the vicinity of the surface of the object to be treated without increasing the humidity in the vicinity of the plasma actuator.

To allow the humidifying device to have the directivity, a known method can be used appropriately. For example, a method in which, by providing a fan and thereby generating an air flow so as not to disturb the induced flows and the air flow 209, the moisture is transferred in a direction of the air flow, a method in which an appropriate pressure is given to the moisture by using an air pump or the like to eject the moisture in an intended direction, or the like can be used. To prevent the induced flows and the air flow 209 from being disturbed, it is preferable to direct the humidifying device in the same direction (first direction) as the direction of each of the induced flows and the air flow 209.

<Arrangement of Plasma Actuator, Ozone Decomposing Device, and Object to be Treated>

In the active oxygen supply device 100, a position of the plasma actuator that causes the induced flows containing the ozone is not particularly limited as long as the plasma actuator is positioned such that, due to the UV light emitted from the UV light source 102, which is the ozone decomposing device, the air flow 209 flows out from the opening portion to the outside of the housing to be supplied to the surface of the object to be treated in a state where the effective active oxygen concentration or effective active oxygen amount according to the object of the treatment is maintained. The same applies also to a case where the ozone decomposing device is the heating device or the humidifying device.

For example, the plasma actuator and the ozone decomposing device may appropriately be arranged such that the air flow 213 containing the generated active oxygen is supplied at the shortest distance to the surface of the object to be treated.

Alternatively, for example, the plasma actuator may appropriately be positioned such that a to-be-treated surface of a to-be-treated object 401 is included in an extension line of a direction extending from the edge portion of the first electrode 203 of the plasma actuator in the first direction along the first surface (the exposed portion 201-1 thereof) of the dielectric material. For example, the extension line is preferably in contact with the to-be-treated surface of the to-be-treated object 401.

In addition, an extension line of the direction (the same as an arrow-X direction) extending from the edge portion of the first electrode 203 of the plasma actuator in the first direction along the first surface of the dielectric material is preferably directed to face the opening. This allows the air flow to easily flow out from the opening portion to the outside of the housing.

By arranging the plasma actuator and the ozone decomposing device as described above, it is possible to locally supply the air flow containing the active oxygen and having a certain flow rate to a region in the vicinity of the surface of the to-be-treated object or treat the region in the vicinity of the surface of the to-be-treated object with the active oxygen.

Moreover, since a distance between the ozone decomposing device and the plasma actuator varies depending on the object of the treatment, the distance therebetween cannot generally be defined. For example, a distance between a surface of the dielectric material of the plasma actuator which faces the ozone decomposing device and the ozone decomposing device is set preferably to 15 mm or less, more preferably to 10 mm or less, or still more preferably to 4 mm or less. However, the plasma actuator need not be placed at a position within about 15 mm from the ozone decomposing device. As long as the active oxygen is allowed to have an effective concentration according to the object of the treatment in relation to an element that may decompose the ozone, such as the illuminance or wavelength of the UV light, the distance between the ozone decomposing device and the plasma actuator is not particularly limited.

Relative positions of the active oxygen supply device and the object to be treated are appropriate as long as at least one of the active oxygen supply device and the object to be treated is disposed such that active oxygen is generated in the air flow, and the surface of the object to be treated is exposed to the air flow in which the effective active oxygen concentration or effective active oxygen amount according to the object of the treatment is maintained.

When the ozone decomposing device is the UV light source, the UV light source may be either disposed at a position where the surface of the object to be treated can be irradiated with UV light or disposed at a position where the surface of the object to be treated cannot be irradiated with the UV light. Even when the surface of the object to be treated cannot be irradiated with the UV light from the UV light source, the treatment device using the active oxygen according to the present embodiment can treat the surface to be treated through the exposure of the surface to be treated to the active oxygen in the air flow.

In the same manner as when the ozone decomposing device is the heating device also, the heating device may be either disposed at a position where the surface of the object to be treated can be heated or disposed at a position where the surface of the object to be treated cannot be heated.

In sterilization treatment using the UV light, what is sterilized is only the surface irradiated with the UV light. However, in the sterilization treatment using the active oxygen supply device according to the present disclosure, bacteria present at a position that can be reached by the active oxygen can be sterilized. Accordingly, for example, even bacteria present between fibers, which is hard to sterilize with UV light irradiation from the outside, may be sterilized.

Figure 6:
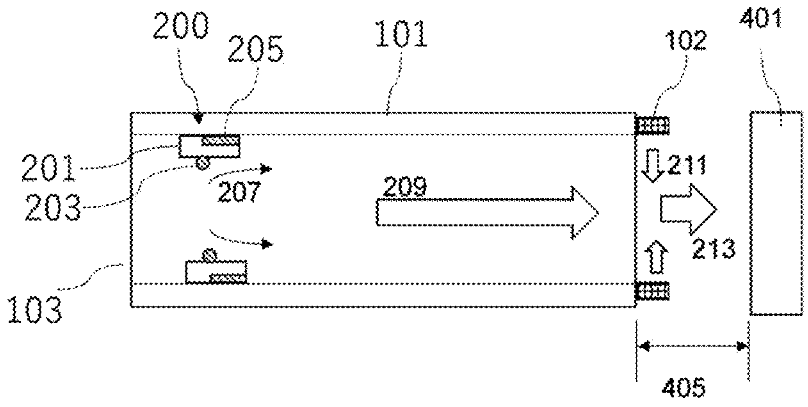
FIG. 6 is a schematic diagram of the active oxygen supply device according to an embodiment of the present disclosure.

Meanwhile, as illustrated in FIG. 6, when the UV light source is disposed so as to allow the UV light therefrom to irradiate the surface of the object to be treated which is placed outside of the housing via the opening portions, the undecomposed ozone present in the air flow 209 can be decomposed in situ on the surface to be treated to be able to generate active oxygen on the surface to be treated. As a result, it is possible to further increase a level of the treatment and the efficiency of the treatment.

In this case, the illuminance of the UV light at the surface of the object to be treated or the illuminance of the UV light in the opening portions is not particularly limited but, even at or in, e.g., the surface of the object to be treated or the opening portions also, it is preferable to set the illuminance of the UV light which can decompose the ozone contained in the air flow 209, generate active oxygen in the air flow 209, and provide the effective active oxygen concentration or effective active oxygen amount according to the object of the treatment. Specifically, for example, a specific example of the illuminance of the UV light at the surface of the object to be treated or the illuminance of the UV light in the opening portions is preferably 40 $\mu W/cm^2$ or more, more preferably 100 $\mu W/cm^2$ or more, still more preferably 400 $\mu W/cm^2$ or more, or particularly preferably 1000 $\mu W/cm^2$ or more. The upper limit of the illuminance is not particularly limited, but can be set to, e.g., 10000 $\mu W/cm^2$ or less.

Meanwhile, a distance between the ozone decomposing device and the surface of the object to be treated also varies depending on the object of the treatment, and accordingly cannot generally be defined, but is set preferably to, e.g., 10 mm or less, or more preferably to 4 mm or less. However, the object to be treated need not be placed such that the surface to be treated of the object to be treated is present at a position within about 10 mm from the ozone decomposing device. As long as the active oxygen in the air flow 209 can be set to the effective concentration according to the object of the treatment in relation to the element that can decompose the ozone, such as the illuminance of the UV light, the distance between the ozone decomposing device and the object to be treated is not particularly limited.

An amount of ozone generated per unit time in the plasma actuator in a state where the ozone in the air flow 209 is kept from being decomposed by the ozone decomposing device is, e.g., preferably 15 μg/minute or more, or more preferably 30 μg/minute or more. An upper limit of the ozone generation amount is not particularly limited, but is, e.g., 1000 μg/minute or less.

A flow rate of the induced flows or the air flow 209 needs only to be, e.g., a speed that allows the generated active oxygen to be positively supplied to the surface region of the object to be treated in the state where the effective active oxygen concentration or effective active oxygen amount according to the object of the treatment is maintained, which is, e.g., about 0.01 m/s to 100 m/s as described above.

As described above, the ozone concentration in the induced flows generated from the plasma actuator and the flow rates of the induced flows can be controlled by using the thicknesses or materials of the electrodes and the dielectric material, the type, amplitude, or frequency of the voltage to be applied, or the like.

<Housing and Opening Portions>

The active oxygen supply device in the present disclosure includes the cylindrical housing 101 having the first opening and the second opening opposite to the first opening, the plasma actuator 200 disposed in the housing, and the ozone decomposing device 102.

The following will describe a preferred mode in the present embodiment, and an arrangement of the first electrode and the second electrode in the housing can be selected appropriately such that, e.g., the generated active oxygen can positively be supplied to the surface region of the object to be treated in the state where the effective active oxygen concentration or effective active oxygen amount according to the object of the treatment is maintained.

The cylindrical housing 101 needs only to be in an embodiment in which the plasma actuator can be attached to the inside thereof and air does not flow in from other than the first opening. Accordingly, a shape, an inner diameter, and an outer diameter of a cross section, a ratio between the inner diameter and the outer diameter, an inner diameter and an outer diameter from the first opening to the second opening, a ratio between the inner diameter and the outer diameter, an amount of change in a cross-sectional shape, a coaxiality of the first opening and the second opening, an angle of refraction of the cylindrical housing 101, a material of the housing, and the like are not particularly limited.

A configuration which does not disturb laminar flow of the induced flows and the air flow 209 each containing the ozone or the induced flows and the air flow 209 each containing the active oxygen is preferred. For example, a structure in which no obstacle is present between an extension line of the direction extending from the edge portion of the first electrode of the plasma actuator along the exposed portion 201-1 of the first surface of the dielectric material and the second opening is preferred.

The length of the cylindrical housing 101 can appropriately be selected, but an air flow of air flowing in from the first opening is easily regulated along the induced flows generated by the plasma actuator. Therefore, a distance between the first opening and the plasma actuator preferably has a length that can be set longer than a distance between the second opening and the plasma actuator.

A cross-sectional shape of the cylindrical housing 101 of the active oxygen supply device in a direction perpendicular to a direction extending from the first opening to the second opening can be selected appropriately from among a polygonal shape such as a quadrilateral shape, a circular shape, an ellipsoidal shape, a combination of the circular shape and the polygonal shape, and the like. For example, the cross-sectional shape is preferably the circular shape or a square shape. In other words, the cylindrical housing preferably has a cylindrical shape or a quadrilateral cylindrical shape. Since it may disturb the laminar flow of the induced flows containing the ozone, a cross-sectional shape or a shape in which a phase of a cross-section shape does not vary while the induced flows 207 are moving forward from the first opening to the second opening is preferred.

A structure in which the inner diameter of the cylindrical housing 101 gradually decreases with distance from the first opening 103 to the second opening is preferable, since a degree of joining together of the induced flows 207 increases to allow a driving force of the active oxygen flowing out from the second opening to be further improved.

To prevent progress of the induced flows and the air flow 209 from the first opening to the second opening from being disturbed, the material and thickness of the cylindrical housing 101 need only to be a material and a thickness which prevent the housing 101 from being deformed under a weight thereof, such as a metal, a ceramic, or a resin. Preferably, the material and thickness of the housing 101 are a highly insulating material and a thickness which prevent leakage from the electrodes of the plasma actuator to the outside.

A method of producing the cylindrical housing 101 is preferably a method which does not allow a portion through which air from the outside flows in to be formed other than the first opening. Specifically, the cylindrical housing 101 may also be a hollow housing molded by injection molding or extrusion molding, a housing obtained by hollowing a solid housing produced by the same production method by means of cutting or the like, a housing obtained by rolling a sheet and then bonding joints with no gap, or the like.

A length from the first opening to the second opening in the cylindrical housing may appropriately be changed according to the object of the treatment, and is not particularly limited, but is, e.g., preferably 3 to 1000 mm, more preferably 5 to 100 mm, or still more preferably 10 to 50 mm.

A size of the opening portion of the first opening, relative positions of centers of the opening and the cylindrical housing, and a shape of the opening are not limited as long as, as a result of changing of the gas in the housing into an air flow due to the induced flows generated by the plasma actuator 200 and movement of the air flow toward the second opening, the first opening is within a range that allows air to flow in from the outside of the first opening. In addition, a lid that controls the shape and size of the first opening may also be provided within a range that does not interfere with an effect of the present embodiment. Among them, to suppress air turbulence, the first opening preferably has the same shape as that of a cross section of an inner circumference of the cylindrical housing.

The inner diameter of the first opening may appropriately be changed depending on the object of the treatment, and is not particularly limited. To stabilize the induced flows generated by the plasma actuator 200, it is preferable to increase, of a flow rate of air flowing in from the first opening, a flow rate which contributes to an intake air flow into the plasma actuator 200. Accordingly, a maximum diameter of the opening portion of the first opening is preferably 5 to 100 mm, or more preferably 10 to 50 mm.

A size of the opening portion of the second opening, relative positions of centers of the opening and the cylindrical housing, a shape of the opening portion, relative positions of the opening portion and the object to be treated are not limited as long as the second opening in is an embodiment in which the air flow 209 generated from the plasma actuator 200 is caused to flow to the outside of the second opening of the cylindrical housing 101. In addition, a lid that controls the shape and size of the second opening may also be provided within a scope that does not interfere with an effect of the present embodiment. For example, the inner diameter of the second opening may appropriately be changed depending on the object of the treatment, and is not particularly limited, but a maximum inner diameter of the second opening can be set preferably to 5 to 100 mm, or more preferably to 10 to 50 mm.

A configuration of the plasma actuator 200 may be either continuous or cut at a plurality of positions in the circumferential direction or the longitudinal direction of the cylindrical housing as long as the plasma actuator 200 is in an embodiment in which the air flow 209 containing the ozone can be generated toward the second opening. For example, from a viewpoint of generating the regulated air flow, providing the plasma actuators equidistantly in the circumferential direction in a cross section perpendicular to the longitudinal direction of the housing is also a preferred embodiment.

Among them, the plasma actuator is preferably configured continuously over the inner circumferential surface around the entire circumference in the circumferential direction, since this can increase the driving force of the air flow 209. Meanwhile, disposing the plasma actuators at a plurality of positions (e.g., two to four positions) in the direction (longitudinal direction) from the first opening to the second opening of the cylindrical housing and between the first opening and the second opening is also preferable in terms of increasing the driving force. The plasma actuator is further preferably provided in a helical shape over the inner surface of the housing, since this can continuously improve the driving force of the air flow 209 inside of the cylindrical housing. It is also preferable to provide the plasma actuator over the inner surface of the housing into a helical shape having a plurality of windings (e.g., two to four windings).

A plurality of the cylindrical active oxygen supply devices according to the present disclosure may also be used in a bundle.

The active oxygen supply device in the present disclosure can be used not only for an application in which the object to be treated is sterilized, but also for all the applications that are implemented by supplying the active oxygen to the object to be treated. For example, the active oxygen supply device in the present disclosure can be used also for an application in which the object to be treated is deodorized, an application in which the object to be treated is bleached, hydrophilization surface treatment for the object to be treated, or the like.

Meanwhile, the treatment device using active oxygen in the present disclosure can be used not only for treatment of sterilizing the object to be treated, but also for, e.g., treatment of deodorizing the object to be treated, treatment of bleaching the object to be treated, a surface treatment of hydrophilizing the object to be treated, or the like.

Note that, in the present disclosure, the "effective active oxygen concentration or effective active oxygen amount" refers to an active oxygen concentration or active oxygen amount for attaining an object with respect to the object to be treated such as, e.g., sterilization, deodorization, bleaching, or hydrophilization, and can be adjusted appropriately according to the object by using the thicknesses and materials of the electrodes and the dielectric material which are included in the plasma actuator, the type, amplitude, and frequency of the voltage to be applied, a degree of ozone decomposition (the illuminance and irradiation time of the UV light, the heating temperature, the heating time, a humidification moisture amount, and a humidification time) by the ozone decomposing device, or the like.

Second Embodiment

Figure 7A:
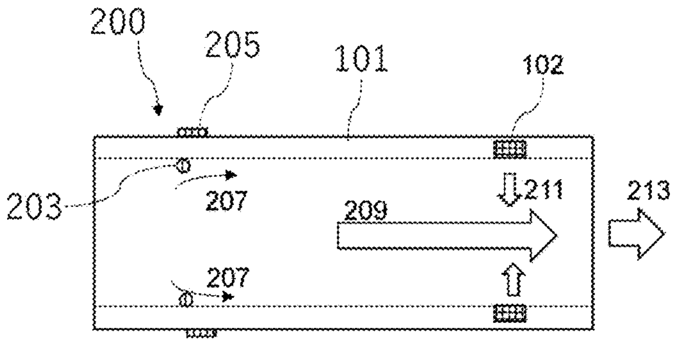
FIGS. 7A to 7C are schematic diagrams of an active oxygen supply device according to another embodiment of the present disclosure.
Figure 7B:
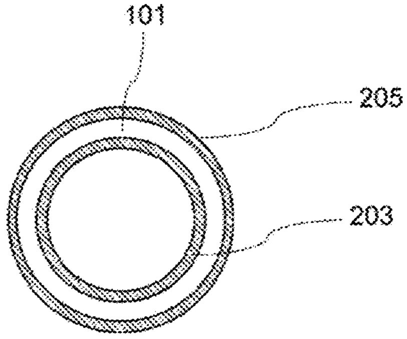
Figure 7C:
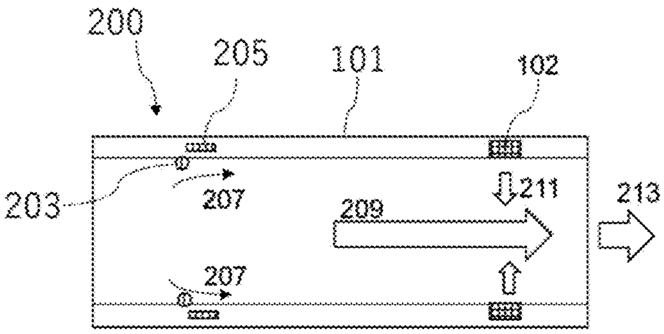

FIGS. 7A to 7C illustrate the second embodiment of the active oxygen supply device according to the present disclosure.

The active oxygen supply device according to the present embodiment includes the cylindrical housing 101, which is a tube, and the cylindrical housing 101 includes the dielectric material.

In a cross section in a direction along an axial direction of the cylindrical housing, on the inner surface of the housing, the first electrode 203, which is the exposed electrode provided to cover a portion of the inner surface, is disposed. In addition, externally of the inner surface of the cylindrical housing 101, the second electrode 205 electrically insulated from the first electrode 203 via the dielectric material is disposed. In other words, the active oxygen supply device in the second embodiment is different from the active oxygen supply device according to the first embodiment in that the cylindrical housing is used as the dielectric material portion of the plasma actuator.

It is not necessary for the entire cylindrical housing to be the dielectric material, and it is sufficient to electrically insulate the first electrode 203 and the second electrode 205 from each other and form, of the dielectric material, a portion that allows the induced flows, which are the unidirectional jet streams, to be generated from the first electrode 203. In other words, a portion not affecting the generation of the induced flows may also be formed of a material other than the dielectric material. Preferably, the cylindrical housing 101 is formed of the dielectric material.

As an example related to positioning of the first electrode 203, as illustrated in FIG. 7B obtained by viewing the active oxygen supply device 100 from the first opening side, a case can be listed where the first electrode 203 is positioned around the entire circumference in the circumferential direction of the inner circumferential surface of the cylindrical housing 101, while the second electrode 205 is positioned around the entire circumference in a circumferential direction of an outer circumferential surface of the cylindrical housing 101. However, the positioning is not limited thereto, and the first electrode 203 may also be disposed either at one position or at each of a plurality of positions in the circumferential direction.

As for positioning of the second electrode 205, when the first electrode 203 is provided around the entire circumference in the circumferential direction as described above, it is preferable to also provide the second electrode around the entire circumference in the circumferential direction in terms of the efficiency of induced flow generation, but the positioning of the second electrode 205 is not limited thereto. As long as the induced flows are generated from at least one portion of the first electrode, the second electrode 205 may also be disposed at either one position or each of a plurality of positions in the circumferential direction. Furthermore, when the first electrode 203 is disposed at one position or each of a plurality of positions, the second electrode 205 may also be disposed at one position or a plurality of positions correspondingly to the position where the first electrode is disposed.

In the present embodiment, the tube serving as the cylindrical housing 101 is formed as the dielectric material of the plasma actuator, and accordingly the material of the cylindrical housing 101 is a material having a high electrically insulating property. As examples of the dielectric material, resins such as polyimide, polyester, a fluorine resin, a silicone resin, an acrylic resin, and a phenol resin, glass, ceramics, composite materials obtained by mixing these with resins, and the like can be used. Among them, the cylindrical housing 101 is preferably a tube made of a flexible resin in which fire is unlikely to spread even when a current leaks.

More preferably, the dielectric material is the silicone resin. It is possible to achieve both an insulating property and a flexibility at a high level.

When formed on the inner circumferential surface of the tube, the first electrode according to the present embodiment may be formed over the surface of the inner circumferential surface within a range in which the induced flows and the air flow 209 each containing the ozone can be generated, or a portion of the first electrode may also be embedded in the tube.

The second electrode 205 is formed externally of the inner surface of the cylindrical housing 101, and the position thereof is not particularly limited as long as the position is within a range in which the induced flows and the air flow 209 each containing the ozone can be generated. Specifically, as illustrated in, e.g., FIG. 7A, the second electrode 205 may be formed on the surface of the outer circumferential surface of the cylindrical housing or, as illustrated in FIG. 7C, the second electrode 205 may also be partly or entirely embedded in the outer circumferential surface of the cylindrical housing. When the second electrode is formed on the surface of the outer circumferential surface, it is possible to further cover the second electrode on the outer circumferential surface with a substrate made of a dielectric material or the like and prevent the induced flows from being generated from an edge portion of the second electrode.

Furthermore, when the first electrode and the second electrode are formed with respect to the cylindrical housing 101, an operation (cutting or polishing) of changing the thickness of the cylindrical housing 101 may also be performed at positions where the electrodes are to be formed within a range in which the induced flows containing the ozone are appropriately generated.

In the present embodiment, shapes, an arrangement, and the like of the cylindrical housing, the first opening, the second opening, the first electrode and the second electrode of the plasma actuator, the ozone decomposing device such as the UV light source, and other constituent features according to the present disclosure can be configured in the same manner as described in the first embodiment. The dielectric material in the first embodiment can be configured in the present embodiment by being read as the cylindrical housing. For example, a selection can be made appropriately such that the generated active oxygen may positively be supplied to the surface region of the object to be treated in a state where the effective active oxygen concentration or effective active oxygen amount according to the object of the treatment is maintained.

For example, in the same manner as in the first embodiment, it may also be possible to dispose the first electrode over the inner surface of the cylindrical housing into a helical shape and dispose the second electrode externally of the inner surface of the cylindrical housing into a helical shape. Alternatively, the cylindrical housing may also be provided with a structure in which the inner diameter gradually decreases with distance from the first opening toward the second opening.

Third Embodiment

Figure 8:
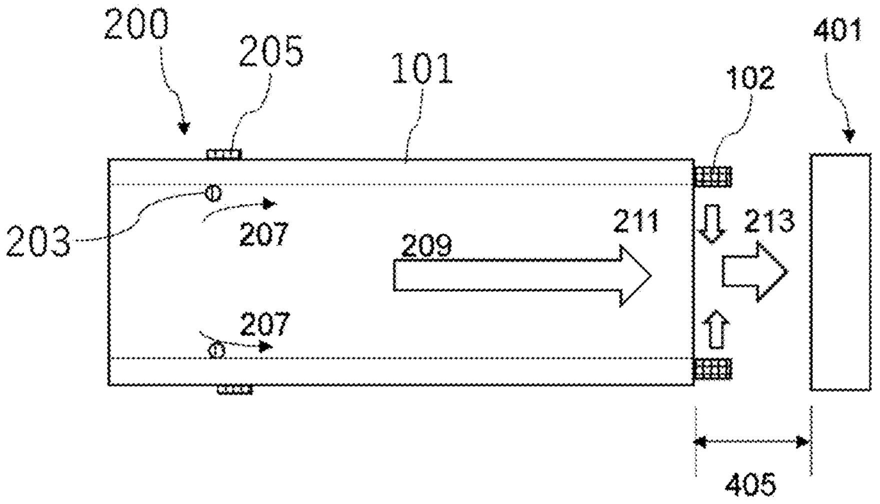
FIG. 8 is a schematic diagram of an active oxygen supply device according to still another embodiment of the present disclosure.

FIG. 8 illustrates the third embodiment of the active oxygen supply device according to the present disclosure.

The active oxygen supply device according to the present embodiment includes the cylindrical housing, which is a tube, the cylindrical housing includes the dielectric material and, on the inner surface of the housing, the first electrode 203, which is the exposed electrode provided to cover a portion of the inner surface, is disposed. In addition, externally of the inner surface of the housing, the second electrode 205 electrically insulated from the first electrode via the dielectric material is disposed. Furthermore, as the ozone decomposing device 102, the UV light source 102 is disposed in the vicinity of the second opening outside of the cylindrical housing 101.

In other words, the active oxygen supply device in the third embodiment is different from the active oxygen supply device according to the second embodiment in that the ozone decomposing device is placed outside of the cylindrical housing.

In the present embodiment, shapes, an arrangement, and the like of the cylindrical housing, the first opening, the second opening, the first electrode and the second electrode of the plasma actuator, the ozone decomposing device such as the UV light source, and other constituent features according to the present disclosure can be configured in the same manner as described in the first and second embodiments. For example, a selection can be made appropriately such that the generated active oxygen may positively be supplied to the surface region of the object to be treated in the state where the effective active oxygen concentration or effective active oxygen amount according to the object of the treatment is maintained.

In the active oxygen supply device according to the present disclosure, when, e.g., an area of the surface to be treated of the object to be treated is large with respect to the openings, it is possible to perform the treatment while moving at least one of the active oxygen treatment device and the object to be treated. Relative moving speeds and movement directions of the active oxygen supply device and the object to be treated at that time may be set appropriately within a range in which the surface to be treated can be treated to an intended degree, and are not particularly limited. In addition, the number of times the object to be treated is treated may similarly be set appropriately within a range in which the surface to be treated can be treated to an intended degree.

EXAMPLES

Using Examples and Comparative Examples, the following will describe the present disclosure in greater detail, but the embodiments of the present disclosure are not limited thereto.

Example 1

1. Production of Active Oxygen Supply Device

To a first surface of a polyimide sheet (having a length of 5 mm, a width of 62.8 mm, and a thickness of 100 μm), which was the dielectric material, aluminum foil having a length of 2.5 mm, a width of 62.8 mm, and a thickness of 100 μm was bonded using an adhesive tape to form the first electrode. Meanwhile, to a second surface of the polyimide sheet also, aluminum foil having a length of 3 mm, a width of 62.8 mm, and a thickness of 100 μm was bonded using an adhesive tape so as to obliquely face the aluminum foil bonded to the first surface and thereby form the second electrode. In addition, the second surface including the second electrode was covered with a polyimide tape so as to prevent the induced flows from being generated from the second electrode. Thus, the plasma actuator including the first electrode and the second electrode which were provided so as to overlap each other over a width of 500 μm with the dielectric material (polyimide sheet) being interposed therebetween was produced.

Then, as a material of the housing 101 of the active oxygen supply device 100, a sheet (having a length of 30 mm, a width of 62.8 mm, and a thickness of 1 mm) made of an ABS resin was prepared. Then, to one surface of the sheet made of the ABS resin, the previously produced plasma actuator was bonded. Specifically, the polyimide sheet side covering the second electrode 205 of the plasma actuator 200 was bonded and fixed. Then, the sheet made of the ABS resin was rolled into a cylindrical shape such that the surface to which the plasma actuator was bonded faced inward to produce the cylindrical housing having the plasma actuator fixed to the inner circumferential surface around the entire circumference, which is illustrated in FIG. 2A and FIG. 2B.

The cylindrical housing 101 had the first opening 103 and the second opening (not shown). Note that the distance from the first opening to the second opening was 30.0 mm. Meanwhile, the length from the first opening 103 to the first-opening-side end portion of the plasma actuator was 15.0 mm. The plasma actuator was placed such that the direction in which the induced flows 207 containing the ozone which was generated from the vicinity of the first electrode 203 were blown out faced the second opening.

In addition, at positions on the inner circumferential surface of the housing 101 where the air flow 209 containing the ozone passed through, the four UV light sources 102 (UV-C LED, Trade Name: ZEUBE 265-2CA, manufactured by Stanley Electric Co., Ltd., peak wavelength=265 nm) were arranged at positions each 5 mm away from the second opening of the cylindrical housing 101 and every 900 in the circumferential direction. The UV light sources 102 were placed such that the distance between each of the UV light sources 102 and the dielectric material 201 of the plasma actuator was 10 mm and the distance between the UV light source and a surface of a flat plate facing the UV light source when the flat plate was brought into contact with the second opening of the housing 101 was 5 mm. Thus, the active oxygen supply device 100 according to the present embodiment was produced.

At a position of the second opening serving as a feeding port for the active oxygen in this active oxygen supply device 100, a spectral radiometer (Trade Name: USR-45D, manufactured by Ushio Inc.) was placed to apply a voltage of 7 V to each of the UV light sources 102 and measure the illuminance of the UV light. From an integration value of spectrum, 600 $\mu W/cm^2$ was determined. At this time, the plasma actuator was not turned ON so as not be affected by blocking of the UV light by the ozone generated from the plasma actuator. Since the object to be treated was placed at, e.g., the position of the second opening, the illuminance of the UV light measured under such conditions was regarded as the illuminance of the UV light at the surface of the object to be treated.

Subsequently, to calculate an amount of the ozone generated from the plasma actuator 200, the active oxygen supply device 100 was placed in an airtight container (not shown) having a volume of 1 liter. The airtight container was provided with an aperture portion that could be sealed with a rubber plug to allow a gas inside to be sucked with an injector from the aperture portion. Then, to the plasma actuator 200, a voltage of 2.4 kVpp having a sine waveform with a frequency of 80 kHz was applied without lighting the UV lamps and, after one minute, 100 ml of the gas inside of the airtight container was collected. An ozone detector tube (Trade Name: 182SB, manufactured by Komei Rikagaku Kogyo Co., Ltd.) was caused to suck the collected gas to determine a measured ozone concentration (PPM) contained in the induced flows from the plasma actuator 200. Using the value of the measured ozone concentration, the amount of ozone generated per unit time was determined on the basis of the following expression:

$$\text{Amount of ozone generated per unit time (mg/minute)} = \text{Measured ozone concentration}(PPM) * \frac{\text{Ozone molecular weight } 48}{22.4} * \frac{\frac{273}{273 + \text{Room temperature } (^\circ\text{ C.})}}{10000} * \frac{\text{Gas in airtight container}(L)}{\text{Collected gas }(L)} = \text{Measured ozone concentration}(PPM) * 48/22.4 * 273/(273+25)/10000 * 0.1/1$$

As a result, the amount of ozone generated per unit time was 130 μg/minute.

Finally, the ozone generation amount when both of the plasma actuator 200 and the UV lamps 102 were operating was measured. An operation condition for the plasma actuator 200 was such that, when only the plasma actuator 200 was operated, 130 μg/minute of ozone was generated. Meanwhile, an operation condition for the UV lamps 102 was such that, when a voltage of 7 V was applied to each of the UV light sources 102 and only the UV lamps 102 were operated, the illuminance was 600 $\mu W/cm^2$. As a result, the ozone generation amount when both of the plasma actuator 200 and the UV lamps 102 were operating was 10 μg/minute. It can be considered that 120 μg/minute corresponding to a decrease from 130 μg/minute was the amount of ozone that had changed to the active oxygen.

2-1. Active Oxygen Detection Test

The presence or absence of the active oxygen in the air flows flown out from the second opening was confirmed using decoloring of methylene blue (see Masanobu WAKASA et al., "Magnetic Field Effect on the Photocatalytic Reaction with $TiO_2$ Semiconductor Film", Journal of The Society of Photographic Science and Technology of Japan, 69, 4, 271-275 (2006) 1). The methylene blue is a crystalline powder with a blue luster and is soluble in water and ethanol, and is therefore used as a dyeing agent or an indicator in a state of a solution. The methylene blue reacts with the active oxygen to be decomposed, and loses blue color. Accordingly, the presence or absence of the active oxygen in the induced flows can be confirmed on the basis of the decoloring (disappearance of blue color) of the methylene blue.

Specifically, the following operation was performed. The methylene blue (manufactured by Kanto Chemical Co., Inc., special grade) and distilled water were mixed to prepare a 0.01% aqueous methylene blue solution. 15 ml of the aqueous methylene blue solution was placed in a petri dish (AB4000 manufactured by Eiken Chem Co., Ltd. and having an 88 mm diameter cylindrical shape). Then, a liquid surface of the aqueous methylene blue solution in the petri dish was regarded as a to-be-treated surface 104-1 of the to-be-treated object, and the active oxygen supply device 100 was placed on the petri dish such that the distance 405 in FIG. 4A was 1 mm.

Then, between the two electrodes of the active oxygen supply device, a 2.4 kVpp ac voltage having a sine waveform with a frequency of 80 kHz was applied, while a 7 V voltage was applied to each of the UV light sources 102, which were the UV lamps 102, to light the UV lamps 102, and the induced flows flown out from the openings were supplied toward the liquid surface for 20 minutes.

The aqueous methylene blue solution after the irradiation of the induced flows was moved from the petri dish to a cell, and changes in an amount of light absorbed in the methylene blue were measured using a spectrophotometer (Trade Name: V-570 manufactured by JASCO Corporation). Since the methylene blue exhibits strong absorption at a wavelength of 664 nm, a degree of decoloring of the methylene blue can be calculated from changes in absorbance at the wavelength. In the present test, first, only the distilled water was placed in a reference cell, and a 0.01% aqueous methylene blue solution before the irradiation of the induced flows was placed in a sample cell, and an absorbance thereof was measured to be 2.32 Abs. Meanwhile, the absorbance of the aqueous methylene blue solution after the irradiation of the induced flows was 0.05 Abs. Accordingly, a ratio of the post-treatment absorbance to the pre-treatment absorbance of the methylene blue at the wavelength of 664 nm was $0.05 \div 2.32 \times 100 = 2\%$.

2-2. Treatment (Sterilization) Test

Using the active oxygen supply device 100, an *Escherichia coli* sterilization test was carried out according to the following procedure. Note that all the instruments used in this sterilization test were sterilized with high-pressure steam using an autoclave. The present sterilization test was performed in a clean bench.

First, *Escherichia coli* (Trade Name "KWIK-STIK (*Escherichia coli* ATCC8739)", manufactured by Microbiologics, Inc.) was placed in a conical flask containing an LB medium (distilled water was added to 2 g of tryptone, 1 g of yeast extract, and 1 g of sodium chloride until reaching 200 ml) and cultured with shaking at 80 rpm at 37° C. for 48 hours. The cultured coliform solution was $9.2 \times 10^9$ (CFU/ml).

A sample No. 1 was produced by dropping 0.010 ml of the cultured bacterial solution onto a qualitative filter paper sheet (Product Number: No. 5C, manufactured by Advantec Co., Ltd.) having a length of 3 cm and a width of 1 cm by using a micropipette. The bacterial solution was dropped only onto one surface of the filter paper sheet. Sample No. 2 was similarly produced.

Then, Sample No. 1 was immersed for 1 hour in a test tube containing 10 ml of a buffer solution (Trade Name: Gibco PBS, manufactured by Thermo Fisher Scientific Inc.). Note that, to prevent the bacterial solution on the filter paper sheet from drying, the time from the dropping of the bacterial solution onto the filter paper sheet to the immersion into the buffer solution was set to 60 seconds.

Next, 1 ml of the buffer solution (hereinafter referred to also as the "1/1 solution") after the immersion of Sample No. 1 therein was placed in a test tube containing 9 ml of the buffer solution to prepare a diluted solution (hereinafter referred to as the "1/10 diluted solution"). A 1/100 diluted solution, a 1/1000 diluted solution, and a 1/10000 diluted solution were prepared in the same manner, except that the dilution ratio with the buffer solution was changed.

Then, 0.050 ml was sampled from the 1/1 solution, and smeared on a stamp medium (PETAN CHECK 25 PT1025, manufactured by Eiken Chemical Co., Ltd.). This operation was repeated to prepare two stamp media smeared with the 1/1 solution. The two stamp media were placed in a thermostat (Trade Name: IS600, manufactured by Yamato Scientific Co., Ltd.) and cultured at a temperature of 37° C. for 24 hours. The numbers of colonies generated in the two stamp media were counted, and an average value thereof was calculated.

For each of the 1/10 diluted solution, the 1/100 diluted solution, the 1/1000 diluted solution, and the 1/10000 diluted solution also, two smeared stamp media were produced and cultured in the same manner as described above. Then, the numbers of colonies generated in the two stamp media were counted, and an average value thereof was calculated. Table 1-1 shows the results.

TABLE 1-1

| | Sample No. 1 (Blank) |
|---|---|
| 1/1 solution | >100 |
| 1/10 solution | >100 |
| 1/100 solution | 54 |
| 1/1000 solution | 5 |
| 1/10000 solution | 0 |

From the results shown in Table 1-1 above, it was found that the number of the colonies when the 1/100 diluted solution was cultured was 54, and therefore the number of bacteria present in 0.050 ml of the 1/1 solution related to Sample No. 1 was $54 \times 10^2$ 5400 (CFU).

Next, the following operation was performed with respect to Sample No. 2.

In a center of a plastic flat plate having a length of 30 cm, a width of 30 cm, and a thickness of 5 mm, a depressed portion having a length of 3.5 cm, a width of 1.5 cm, and a depth of 1.4 mm was provided. A filter paper sheet having a length of 3.5 cm and a width of 1.5 cm was laid in the depressed portion. On the filter paper sheet, Sample No. 2 was placed such that the bacterial-solution-dropped lower surface thereof faced the filter paper sheet laid on a bottom portion of the depressed portion. Then, on an upper surface of the plastic plate, the active oxygen supply device was placed such that a center of the opening thereof coincided with a center of the depressed portion in the longitudinal direction. At this time, the distance 405 illustrated in FIG. 4A was set to 5 mm.

Then, between the two electrodes of the plasma actuator, a 2.4 kVpp ac voltage having a sine waveform with a frequency of 80 kHz was applied, while a 7 V voltage was applied to the UV lamps to light the UV lamps and supply the induced flows toward the filter paper sheet. A supply time (treatment time) was set to 2 seconds.

In a treatment process using the active oxygen supply device, to prevent the filter paper sheet to which the bacterial solution was dropped from drying, the time from the dropping of the bacterial solution onto the filter paper sheet to the immersion into the buffer solution was set to 60 seconds. Sample No. 2 after the treatment was immersed together with the filter paper sheet laid on the bottom portion of the depressed portion for 1 hour in a test tube containing 10 ml of a buffer solution (Trade Name: Gibco PBS, available from Thermo Fisher Scientific Inc.). Then, 1 ml of the buffer solution after the immersion (hereinafter referred to also as the "1/1 solution") was placed in a test tube containing 9 ml of the buffer solution to prepare a diluted solution (1/10 diluted solution). A 1/100 diluted solution, a 1/1000 diluted solution, and a 1/10000 diluted solution were prepared in the same manner, except that the dilution ratio with the buffer solution was changed.

Then, 0.050 ml was sampled from the 1/1 solution, and smeared on a stamp medium (Trade Name: PETAN CHECK 25 PT1025, manufactured by Eiken Chemical Co., Ltd.). This operation was repeated to prepare two stamp media smeared with the 1/1 solution. A total of the two stamp media were placed in a thermostat (Trade Name: IS600, manufactured by Yamato Scientific Co., Ltd.) and cultured at a temperature of 37° C. for 24 hours. The numbers of colonies generated in the individual stamp media related to the 1/1 solution were counted, and an average value thereof was calculated. For each of the 1/10 diluted solution, the 1/100 diluted solution, the 1/1000 diluted solution, and the 1/10000 diluted solution also, two smeared stamp media were produced and cultured in the same manner as described above. Then, the numbers of colonies generated in the individual stamp media related to each of the diluted solutions were counted, and an average value thereof was calculated. Table 1-2 shows the results.

TABLE 1-2

| | Sample No. 2 |
|---|---|
| 1/1 solution | >100 |
| 1/10 solution | 17 |
| 1/100 solution | 0 |
| 1/1000 solution | 0 |
| 1/10000 solution | 0 |

As shown in Table 1-1 above, the number of bacteria in 0.050 ml of the 1/1 solution related to Sample No. 1 that was not treated with the active oxygen supply device was 5400 (CFU). Meanwhile, the number of bacteria in 0.050 ml of the 1/1 solution related to Sample No. 2 after the treatment was 17×10=170 (CFU). From this, it was found that, by the 7 second treatment using the active oxygen supply device according to the present embodiment, ((5400−170/5400)×100)=96.85% sterilization was achieved.

Example 2

An active oxygen supply device was produced and evaluated in the same manner as in Example 1 except that the material of the dielectric material 201 of the plasma actuator was changed to the silicone resin. The evaluation result is shown in Table 2.

Example 3

Figure 9A:
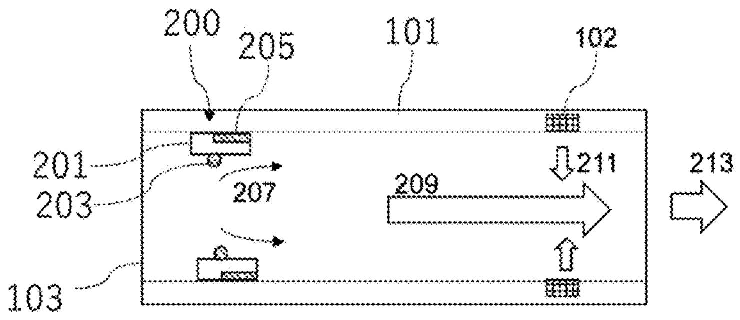
FIG. 9A and FIG. 9B are schematic longitudinal cross-sectional views of an active oxygen supply device according to Example 3.
Figure 9B:
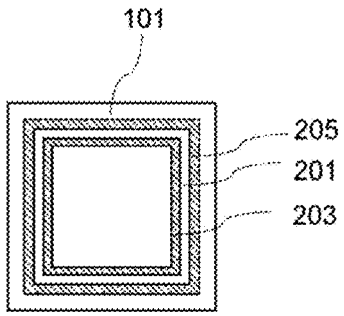

As illustrated in FIG. 9A (longitudinal cross-sectional view) and FIG. 9B (view seen from the second opening), an active oxygen supply device was produced and evaluated in the same manner as in Example 2 except that the cylindrical housing 101 was changed to a housing having a quadrilateral (square) cross-sectional shape. The evaluation result is shown in Table 2. Note that the inner diameter in Table 2 is a length of a diagonal line of the cross-sectional shape.

Example 4

Figure 10:
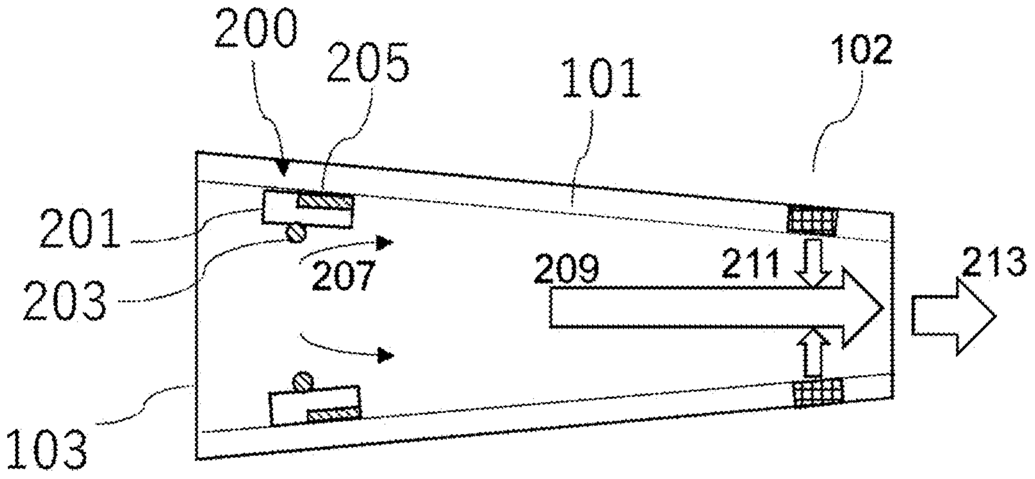
FIG. 10 is a schematic longitudinal cross-sectional view of an active oxygen supply device according to Example 4.

As illustrated in FIG. 10, an active oxygen supply device was produced and evaluated in the same manner as in Example 2 except that the cylindrical housing 101 was changed to a structure in which an inner diameter gradually decreased with distance from the first opening to the second opening, specifically a sheet for forming the cylindrical housing 101 was changed to a sheet having dimensions of a trapezoidal shape (having a length of 30 mm, an upper side of 62.8 mm, a lower side of 31.4 mm, and a thickness of 1 mm), and the evaluation result is shown in Table 2. The cylindrical housing 101 in the present embodiment has a shape in which the inner diameter linearly decreases, while the thickness of the housing is maintained, an inner diameter of the first opening is 20 mm, a shape thereof is a circular shape, an inner diameter of the second opening is 10 mm, and a shape thereof is a circular shape.

Example 5

Figure 11:
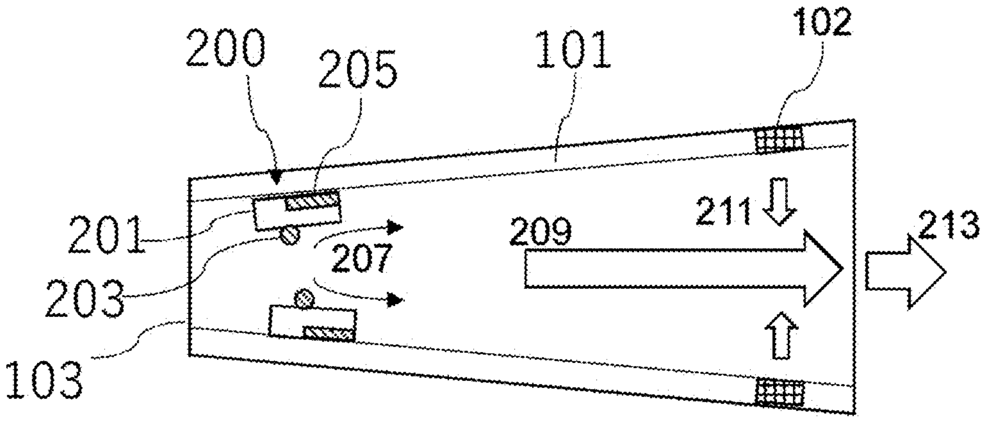
FIG. 11 is a schematic longitudinal cross-sectional view of an active oxygen supply device according to Example 5.

As illustrated in FIG. 11, an active oxygen supply device was produced and evaluated in the same manner as in Example 2 except that the cylindrical housing 101 was changed to a structure in which an inner diameter gradually increased with distance from the first opening to the second opening, specifically a sheet for forming the cylindrical housing 101 was changed to a sheet having dimensions of a trapezoidal shape (having a length of 30 mm, an upper side of 62.8 mm, a lower side of 94.2 mm, and a thickness of 1 mm), and the evaluation result is shown in Table 2. The cylindrical housing 101 in the present embodiment has a shape in which the inner diameter linearly increases, while the thickness of the housing is maintained, an inner diameter of the first opening is 20 mm, a shape thereof is a circular shape, an inner diameter of the second opening is 30 mm, and a shape thereof is a circular shape.

Example 6

As illustrated in FIG. 6, an active oxygen supply device was produced and evaluated in the same manner as in Example 2 except that the UV light source was disposed outside of the cylindrical housing 101, and the evaluation result is shown in Table 2.

Example 7

Figure 12A:
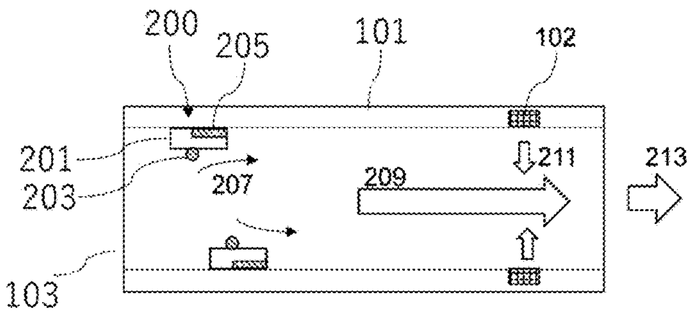
FIGS. 12A to 12C are schematic longitudinal cross-sectional views of an active oxygen supply device according to Example 7.
Figure 12B:
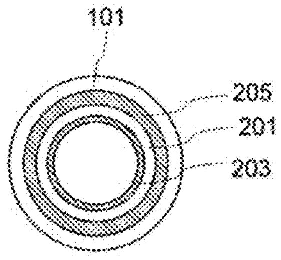
Figure 12C:
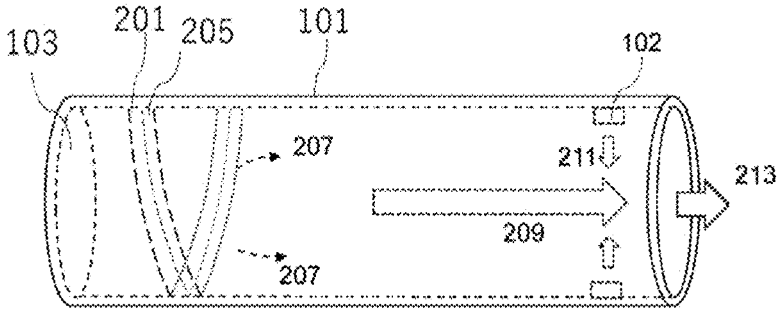

As illustrated in FIG. 12A (longitudinal cross-sectional view), FIG. 12B (view seen from the second opening), and FIG. 12C (perspective view), a belt-like plasma actuator was disposed over the inner circumferential surface of the housing into a one-winding helical shape. An active oxygen supply device was produced and evaluated in otherwise the same manner as in Example 2. The evaluation result is shown in Table 2.

Example 8

Figure 13A:
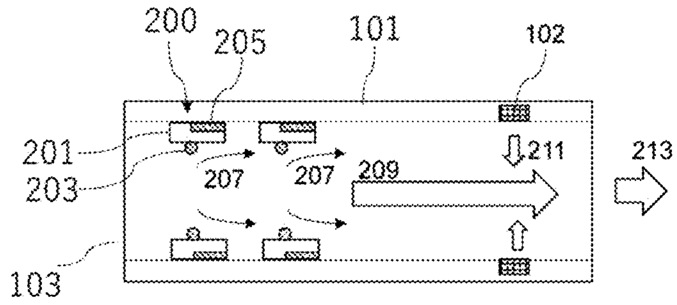
FIGS. 13A to 13C are schematic longitudinal cross-sectional views of an active oxygen supply device according to Example 8.
Figure 13B:
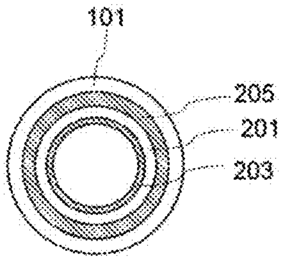
Figure 13C:
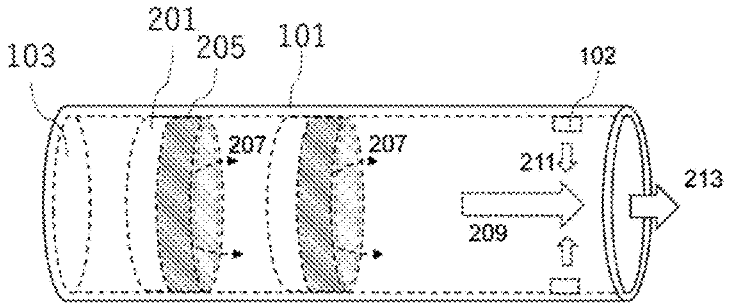

As illustrated in FIG. 13A (longitudinal cross-sectional view), FIG. 13B (view seen from the second opening), and FIG. 13C (perspective view), belt-like plasma actuators were disposed at two positions in the longitudinal direction on the inner circumferential surface of the housing around the entire circumference. An active oxygen supply device was produced and evaluated in otherwise the same manner as in Example 2. The evaluation result is shown in Table 2.

Example 9

Figure 14A:
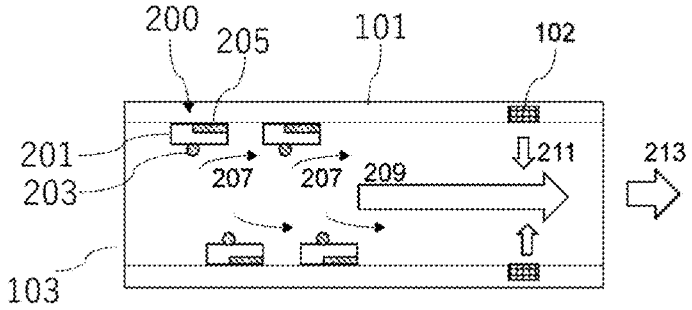
FIGS. 14A to 14C are schematic longitudinal cross-sectional views of an active oxygen supply device according to Example 9.
Figure 14B:
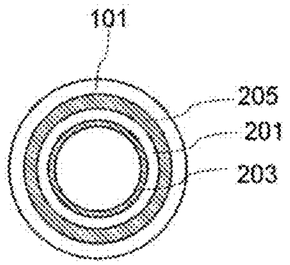
Figure 14C:
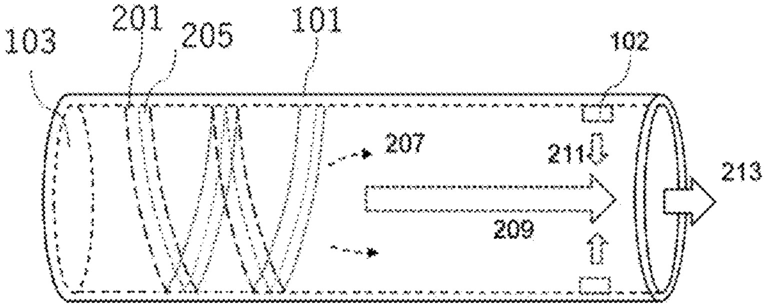

As illustrated in FIG. 14A (longitudinal cross-sectional view), FIG. 14B (view seen from the second opening), and FIG. 14C (perspective view), an active oxygen supply device was produced and evaluated in the same manner as in Example 2 except that a belt-like plasma actuator was disposed over the inner circumferential surface of the housing 101 into a two-winding helical shape. The evaluation result is shown in Table 2.

Example 10

Figure 15A:
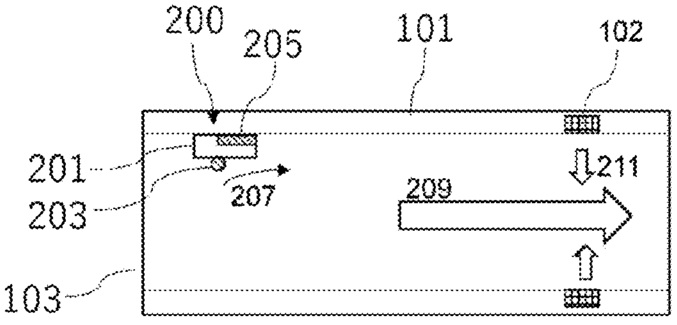
FIGS. 15A to 15C are schematic longitudinal cross-sectional views of an active oxygen supply device according to Example 10.
Figure 15B:
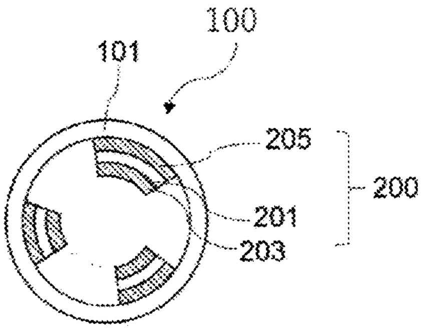
Figure 15C:
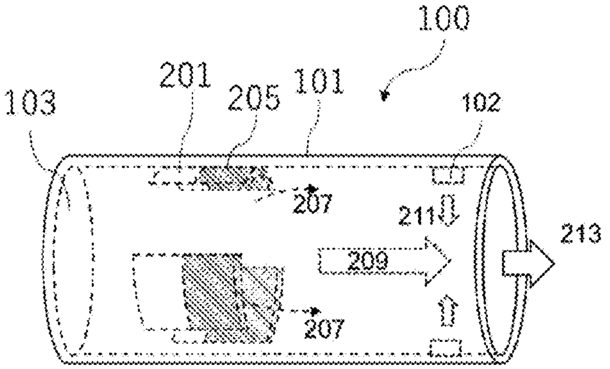

As illustrated in FIG. 15A (cross-sectional view of a portion where a plasma actuator was disposed in the longitudinal direction), FIG. 15B (view seen from the second opening), and FIG. 15C (perspective view), an active oxygen supply device was produced in the same manner as in Example 2 except that plasma actuators were disposed non-continuously at three positions in the circumferential direction. The evaluation result is shown in Table 2.

Example 11

As illustrated in FIG. 7A (longitudinal cross-sectional view) and FIG. 7B (view seen from the second opening), the cylindrical housing 101 was used as the dielectric material of the plasma actuator, the first electrode 203 was disposed over the inner circumferential surface of the housing around the entire circumference, and the second electrode 205 was disposed over the outer circumferential surface of the housing around the entire circumference. Note that an amount of the overlap between the first electrode 203 and the second electrode 205 was set to 200 μm. An active oxygen supply device was produced and evaluated in otherwise the same manner as in Example 2. The evaluation result is shown in Table 2.

Example 12

Figure 16A:
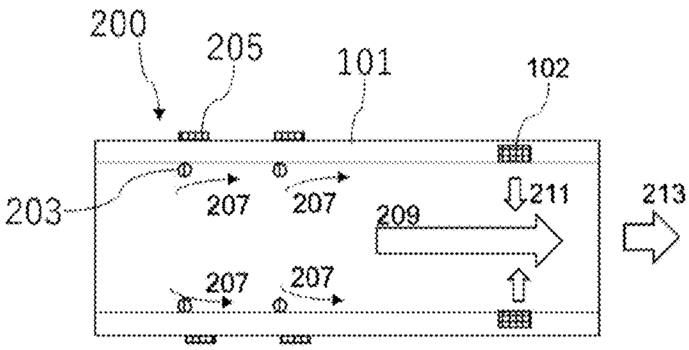
FIGS. 16A to 16C are schematic longitudinal cross-sectional views of an active oxygen supply device according to Example 12.
Figure 16B:
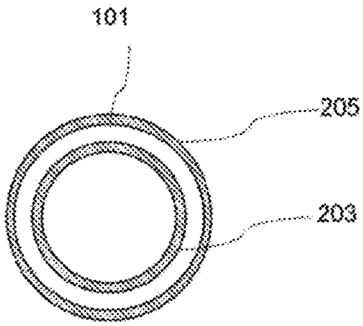
Figure 16C:
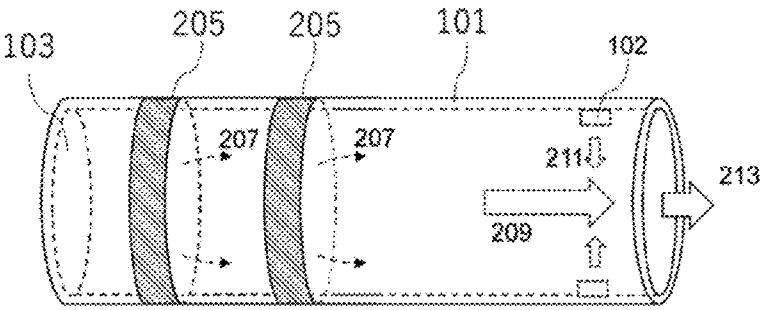

As illustrated in FIG. 16A (longitudinal cross-sectional view), FIG. 16B (view seen from the second opening), and FIG. 16C (perspective view), an active oxygen supply device was produced and evaluated in the same manner as in Example 11 except that the first electrode 203 and the second electrode 205 were disposed at two positions on the inner circumferential surface of the housing (dielectric material) around the entire circumference. The evaluation result is shown in Table 2.

Example 13

Figure 17A:
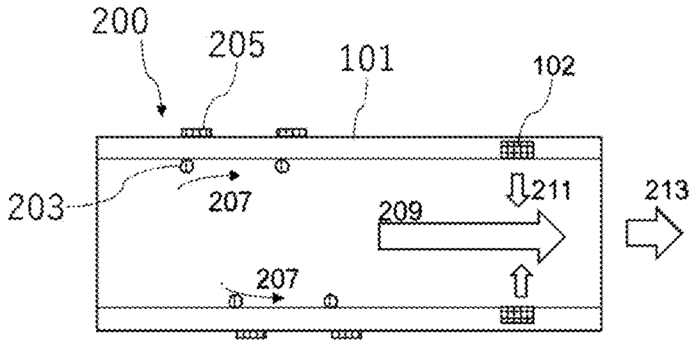
FIG. 17A and FIG. 17B are schematic longitudinal cross-sectional views of an active oxygen supply device according to Example 13.
Figure 17B:
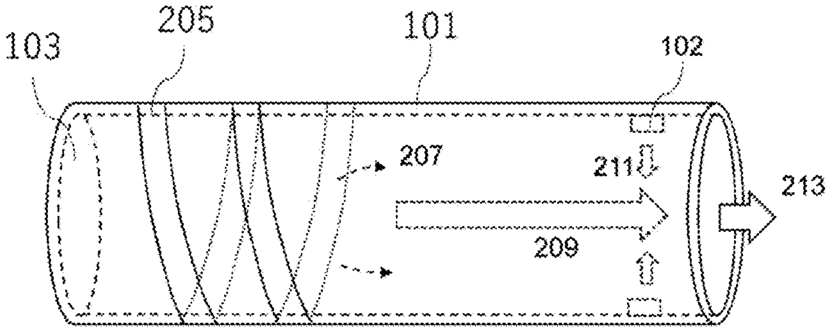

As illustrated in FIG. 17A (longitudinal cross-sectional view) and FIG. 17B (perspective view), the first electrode 203 having a conductive wire shape was disposed over the inner circumferential surface of the housing 101 into a two-winding helical shape. In addition, the belt-like second electrode was disposed at a position on the outer circumferential surface of the housing 101 corresponding to the first electrode into a two-winding helical shape. Note that, in a longitudinal cross-sectional view (FIG. 17A), an amount of the overlap between the first electrode 203 and the second electrode 205 was set to 200 μm. An active oxygen supply device was produced and evaluated in otherwise the same manner as in Example 11, and the evaluation result is shown in Table 2.

Example 14

As illustrated in FIG. 8, an active oxygen supply device was produced and evaluated in the same manner as in Example 11 except that the UV light source was disposed outside of the cylindrical housing 101, and the evaluation result is shown in Table 2.

Comparative Example 1

An active oxygen supply device was produced and evaluated in the same manner as in Example 1 except that, as the ozone generating device, an ozone generator was provided instead of the plasma actuator and that the active oxygen supply device was configured such that air is fed from the first opening by using a fan. The evaluation result is shown in Table 2.

In the present comparative example, by feeding the air from the first opening by using the fan, a turbulent flow occurred in the cylindrical housing, active oxygen was immediately deactivated and did not exhibit the effect of decoloring the methylene blue, and consequently a sterilizing effect significantly deteriorated.

Comparative Example 2

The active oxygen supply device produced in Example 1 was prepared. Then, Evaluation 2-1 and Evaluation 2-2 were performed in the same manner as in Example 1 except that the UV lamps were not operated. The evaluation result is shown in Table 2.

TABLE 2

| Example No. | Cross-Sectional Schematic Diagram No. | Cylindrical Shape Cross-Sectional Shape | First Opening Shape | First Opening Inner Diameter (mm) | Second Opening Shape | Second Opening Inner Diameter (mm) | Dielectric Material | Methylene Blue Absorbance (%) | Sterilization Rate (%) |
|---|---|---|---|---|---|---|---|---|---|
| Example 1 | 1B | Circular | Circular | 20 | Circular | 20 | Polyimide Sheet | 16 | 96.85 |
| Example 2 | 1B | Circular | Circular | 20 | Circular | 20 | Silicone Resin | 15 | 97.28 |
| Example 3 | 9A | Square | Square | 20 | Square | 20 | Silicone Resin | 14 | 97.35 |
| Example 4 | 10 | Circular | Circular | 20 | Circular | 10 | Silicone Resin | 11 | 97.67 |
| Example 5 | 11 | Circular | Circular | 20 | Circular | 30 | Silicone Resin | 20 | 96.57 |
| Example 6 | 6 | Circular | Circular | 20 | Circular | 20 | Silicone Resin | 14 | 97.36 |
| Example 7 | 12A | Circular | Circular | 20 | Circular | 20 | Silicone Resin | 13 | 98.29 |
| Example 8 | 13A | Circular | Circular | 20 | Circular | 20 | Silicone Resin | 8 | 99.30 |

TABLE 2-continued

| Example No. | Cross-Sectional Schematic Diagram No. | Cylindrical Shape Cross-Sectional Shape | First Opening Shape | First Opening Inner Diameter (mm) | Second Opening Shape | Second Opening Inner Diameter (mm) | Dielectric Material | Methylene Blue Absorbance (%) | Sterilization Rate (%) |
|---|---|---|---|---|---|---|---|---|---|
| Example 9 | 14A | Circular | Circular | 20 | Circular | 20 | Silicone Resin | 2 | 99.93 |
| Example 10 | 15A | Circular | Circular | 20 | Circular | 20 | Polyimide Sheet | 19 | 96.57 |
| Example 11 | 7A | Circular | Circular | 20 | Circular | 20 | Silicone Resin (Housing) | 15 | 97.40 |
| Example 12 | 16A | Circular | Circular | 20 | Circular | 20 | Silicone Resin (Housing) | 8 | 99.20 |
| Example 13 | 17A | Circular | Circular | 20 | Circular | 20 | Silicone Resin (Housing) | 2 | 99.91 |
| Example 14 | 8 | Circular | Circular | 20 | Circular | 20 | Silicone (Housing) | 16 | 97.20 |
| Comparative Example 1 | — | Circular | Circular | 20 | Circular | 20 | — | 45 | 81.04 |
| Comparative Example 2 | 18 | Circular | Circular | 20 | Circular | 20 | Polyimide Sheet | 87 | 32.17 |

Note that the values in the column "Methylene Blue Absorbance (%)" in the table are values based on 100% as a value when induced flows are not irradiated.

The present disclosure is not limited to the embodiments above, and can accommodate various modifications and alterations without departing from the spirit and scope of the disclosure. Accordingly, the claims below are appended herein to for the purpose of making public the scope of the present disclosure.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An active oxygen supply device comprising:

a cylindrical housing having a first opening and a second opening opposite to the first opening;

a plasma actuator disposed in the housing; and an ozone decomposing device, wherein the plasma actuator has a first electrode, a dielectric material, and a second electrode, the dielectric material is interposed between the first electrode and the second electrode to electrically insulate the first electrode and the second electrode from each other, the first electrode is an exposed electrode provided on a first surface, which is one surface of the dielectric material, the plasma actuator causes a dielectric barrier discharge directed from the first electrode to the second electrode by applying a voltage between the first electrode and the second electrode and causes an induced flow containing ozone to be blown out from the first electrode in a first direction, which is one direction along the one surface of the dielectric material, the plasma actuator is disposed such that a direction in which the induced flow is blown out faces the second opening, and causes the induced flow to cause an air flow directed from the first opening to the second opening inside of the housing, the ozone decomposing device decomposes the ozone contained in the air flow to generate active oxygen in the air flow, and the air flow results in an air flow containing the active oxygen, and the plasma actuator and the ozone decomposing device are arranged such that the air flow containing the active oxygen flows out from the second opening to an outside of the active oxygen supply device.

2. The active oxygen supply device according to claim 1, wherein the plasma actuator is disposed around an entire circumference in a circumferential direction inside of the housing.

3. The active oxygen supply device according to claim 1, wherein the plasma actuator is provided in a helical shape over an inner surface of the housing.

4. The active oxygen supply device according to claim 1, wherein the plasma actuators are disposed at a plurality of positions on the housing between the first opening and the second opening.

5. The active oxygen supply device according to claim 1, wherein the dielectric material is a silicone resin.

6. The active oxygen supply device according to claim 1, wherein the cylindrical housing has a cylindrical shape or a quadrilateral cylindrical shape.

7. The active oxygen supply device according to claim 1, wherein the ozone decomposing device is at least one device selected from the group consisting of:

a UV light source that irradiates the air flow with UV light to generate the active oxygen in the air flow;

a heating device that heats the air flow to generate the active oxygen in the air flow; and a humidifying device that humidifies the air flow to generate the active oxygen in the air flow.

8. An active oxygen supply device comprising:

a cylindrical housing having a first opening and a second opening opposite to the first opening; and an ozone decomposing device, wherein the cylindrical housing includes a dielectric material, in a cross section of the cylindrical housing in a direction along an axial direction thereof, a first electrode, which is an exposed electrode provided to cover a portion of an inner surface of the cylindrical housing, is disposed on the inner surface, while a second electrode electrically insulated from the first electrode via the dielectric material is disposed externally of the inner surface of the housing, the active oxygen supply device causes a dielectric barrier discharge directed from the first electrode to the second electrode by applying a voltage between the first electrode and the second electrode and causes an induced flow containing ozone to be blown out from the first electrode in a direction of the second opening, which is one direction along the inner surface of the housing, the induced flow causes an air flow directed from the first opening to the second opening inside of the cylindrical housing, the ozone decomposing device decomposes the ozone contained in the air flow to generate active oxygen in the air flow, and the air flow results in an air flow containing the active oxygen, and the first electrode, the second electrode, and the ozone decomposing device are arranged such that the air flow containing the active oxygen flows out from the second opening.

9. The active oxygen supply device according to claim 8, wherein the dielectric material is a silicone resin.

10. The active oxygen supply device according to claim 8, wherein the cylindrical housing has a cylindrical shape or a quadrilateral cylindrical shape.

11. The active oxygen supply device according to claim 8, wherein the ozone decomposing device is at least one device selected from the group consisting of:

a UV light source that irradiates the air flow with UV light to generate the active oxygen in the air flow;

a heating device that heats the air flow to generate the active oxygen in the air flow; and a humidifying device that humidifies the air flow to generate the active oxygen in the air flow.

12. An active oxygen supply device comprising:

a cylindrical housing having a first opening and a second opening opposite to the first opening; and an ozone decomposing device, wherein the cylindrical housing includes a dielectric material, in a cross section of the cylindrical housing in a direction along an axial direction thereof, a first electrode, which is an exposed electrode provided to cover a portion of an inner surface of the cylindrical housing, is disposed on the inner surface, while a second electrode electrically insulated from the first electrode via the dielectric material is disposed externally of the inner surface of the housing, the active oxygen supply device causes a dielectric barrier discharge directed from the first electrode to the second electrode by applying a voltage between the first electrode and the second electrode and causes an induced flow containing ozone to be blown out from the first electrode in a direction of the second opening, which is one direction along the inner surface of the housing, the induced flow causes an air flow directed from the first opening to the second opening inside of the cylindrical housing, the first electrode and the second electrode are arranged such that the air flow containing the ozone flows out from the second opening, and the ozone decomposing device decomposes the ozone contained in the air flow flown out from the second opening to cause active oxygen in the air flow.

13. The active oxygen supply device according to claim 12, wherein the dielectric material is a silicone resin.

14. The active oxygen supply device according to claim 12, wherein the cylindrical housing has a cylindrical shape or a quadrilateral cylindrical shape.

15. The active oxygen supply device according to claim 12, wherein the ozone decomposing device is at least one device selected from the group consisting of:

a UV light source that irradiates the air flow with UV light to generate the active oxygen in the air flow;

a heating device that heats the air flow to generate the active oxygen in the air flow; and a humidifying device that humidifies the air flow to generate the active oxygen in the air flow.

* * * * *